US006767541B2

(12) United States Patent
Slamon et al.

(10) Patent No.: US 6,767,541 B2
(45) Date of Patent: Jul. 27, 2004

(54) HER-2/NEU OVEREXPRESSION ABROGATES GROWTH INHIBITORY PATHWAYS

(75) Inventors: Dennis J. Slamon, Woodland Hills, CA (US); Cindy A. Wilson, Los Angeles, CA (US); Frank J. Calzone, Westlake Village, CA (US)

(73) Assignees: The Regents of the University of California, Oakland, CA (US); Amgen Inc., Thousand Oaks, CA (US)

( * ) Notice: Subject to any disclaimer, the term of this patent is extended or adjusted under 35 U.S.C. 154(b) by 59 days.

(21) Appl. No.: 09/813,517

(22) Filed: Mar. 20, 2001

(65) Prior Publication Data

US 2002/0051785 A1 May 2, 2002

Related U.S. Application Data

(60) Provisional application No. 60/190,598, filed on Mar. 20, 2000.

(51) Int. Cl.$^7$ ...................... A61K 39/395; A61K 38/18; A61K 38/19; C07K 16/30; C07K 16/28
(52) U.S. Cl. ................................ 424/143.1; 424/130.1; 424/133.1; 424/141.1; 424/142.1; 424/152.1; 424/155.1; 424/156.1; 424/172.1; 424/174.1; 530/387.1; 530/387.3; 530/387.7; 530/388.1; 530/388.15; 530/388.2; 530/388.22; 530/388.8; 530/388.85; 514/2
(58) Field of Search ........................... 424/130.1, 133.1, 424/135.1, 138.1, 141.1, 142.1, 143.1, 172.1, 174.1, 152.1, 155.1, 156.1; 514/2; 530/387.1, 387.3, 387.7, 388.1, 388.15, 388.2, 388.22, 388.8, 388.85

(56) References Cited

U.S. PATENT DOCUMENTS 5,120,535 A * 6/1992 Marquardt et al.
5,147,854 A * 9/1992 Newman
5,720,954 A * 2/1998 Hudziak et al.

OTHER PUBLICATIONS

Wiener, J.R. et al, Current Opinion in Oncology, 4: 946–954, 1992.*
Lewis, G.D. et al, Cancer Immunol. Immunother., 37: 255–263, 1993.*
Bookman, Seminars in Oncology (1998) 25(3): 381–396.*
S. Ogawa et al., 1996, Oncogene, 13:183–191.
T. Bellon et al., 1993, Eur. J. Immunol., 23:2340–2345.
S.P. Oh et al., 1994, Genomics, 19:494–499.
C. Bartholomew et al., 1997, Oncogene, 14:569–577.
G. Nucifora, 1997, Leukemia, 11:2022–2031.
M.A. Perrella, 1998, Miner Electrolyte Metal, 24:136–143.
G.R. Grotendorst, 1997, Cytokine Growth Factor Rev, 8(3):171–179.
S.-N. Bae et al., 1993, Breast Cancer Res. Treat., 24:241–255.
L. Ala–Kokka et al., 1989, Biochem. J., 260:509–516.
M. Kretzschmar et al., 1999, Genes & Dev., 13:804–816.
E. Piek et al., 1999, J. Cell Science 112:4557–4568.
H.Y. Lin, 1992, Cell, 68:775–785.
H.Y. Lin, 1992, Mol Reprod Dev, 32:105–110.
J. Massague, 1992, Cell, 69:1067–1070.
H. Yamashita et al., 1994, J. Biol. Chem., 269(3):1995–2001.
A. Letamendia et al., 1998, J. Biol. Chem., 273(49):33011–33019.
N.P. Barbara, 1999, J. Biol. Chem., 274(2):584–594.
B.–W. Park et al., 2000, Nat Biotechnol, 18:194–198.
P. Bork, 1993, FEBS Lett, 327(2):125–130.
A. Brunner et al., 1991, DNA Cell Biol, 10(4):293–300.
M.L. Kireeva et al., 1996, Mol Cell Biol, 16(4):1326–1334.
H. Hirai, 1999, Int J Biochem Cell Bio, 31:1367–1371.
M. Kurokawa et al., 1998, Nature, 394:92–96.
A.B. Roberts, 1999, Microbes Infect, 1:1265–1273.
D. Ralph et al., 1993, Proc Natl Acad Sci USA, 90:10710–10714.
P.T. Dijke et al., 1988, Proc Natl Acad Sci, 85:4715–4719.
M.C. Kiefer et al., 1991, Biochem Biophys Res Comm, 176(1):219–255.
D.M. Bradham et al., 1991, J Cell Biol, 114(6):1285–1294.
L. Madisen et al., 1988, DNA, 7(1):1–8.
N. Shimizu et al., 1992, J Biochem, 111:272–277.
K.A. Myers et al., J Biol Chem, 269(12):9319–9324.
A. Ullrich et al., 1986, EMBO J, 5(10):2503–2512.
K. Galaktionov et al., 1991, Cell, 67:1181–1194.
J. Didsbury et al., 1989, J Biol Chem, 264(28):16378–16382.
J. Sukegawa et al., 1987, Mol Cell Biol, 7(1):41–47.
F.V. Straaten et al., 1983, Proc Natl Acad Sci USA, 80:3183–3187.
S. Davis et al., 1996, Cell, 87:1161–1169.
D. Ron et al., 1993, J Biol Chem, 268(8):5386–5394.
A.R. Kornblihtt et al., 1983, Proc Natl Acad Sci USA, 80:3218–3222.
K.L. Gould, 1989, EMBO J, 8(13):4133–4142.

(List continued on next page.)

*Primary Examiner*—Anthony C. Caputa
*Assistant Examiner*—Anne L. Holleran
(74) *Attorney, Agent, or Firm*—Gates & Cooper LLP

(57) ABSTRACT

The present invention provides methods for obtaining genetic profiles of cancer cells in order to assess the status of a cancer in an individual. In addition, the present invention provides methods for inhibiting the growth of cancer cells that exhibit certain genetic profiles. These methods identify an important link between HER-2/neu overexpression and loss of growth inhibition by the TGF-β signaling pathway in cancer cells. Compositions as well as therapeutic and diagnostic methodologies based on this disclosure are provided.

19 Claims, 10 Drawing Sheets

OTHER PUBLICATIONS

C. Wang et al., 1996, Gene, 174:299–306.
A.E. Parker et al., 1991, J Biol Chem, 266(16):10438–10445.
H.-J. Harn et al., 1991, Biochem Biophys Res Commun, 178(3):1127–1134.
R.N. Tamura et al., 1990, J Cell Biol, 111:1593–1604.
K.K. Murthy et al., 1999, J Bio Chem, 274(29):20679–20687.
J.R. Glenney et al., 1992, FEBS Lett, 314(1):45–48.
M.C. Graves et al., 1985, Proc Natl Acad Sci USA, 82:1653–1657.
A.J. Celeste et al., 1990, Proc Natl Acad Sci USA, 87:9843–9847.
J.M. Wozney et al., 1988, Science, 242:1528–1534.
H. Ogasa et al., 1996, Gene, 181:185–190.
J. Skonier et al., 1992, DNA Cell Biol, 11(7):511–522.
W.G. Stetler–Stevenson et al., 1990, J Biol Chem, 265(23):13933–13938.
A. Inoue et al., 1989, J Biol Chem, 264(25):14954–14959.
D.S. Greenspan et al., 1991, J Biol Chem, 266(36):24727–24733.
T. Ny et al., 1986, Proc Natl Acad Sci USA, 83:6776–6780.
N. Chen et al., 2000, J Biol Chem, 275(32):24953–24961.

* cited by examiner

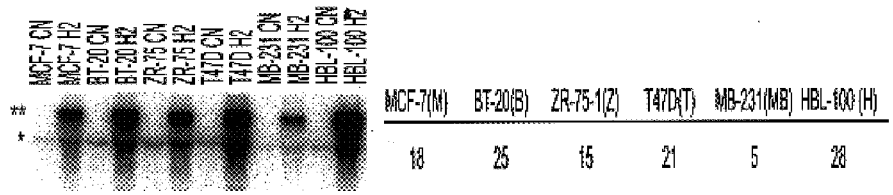
FIG. 2A
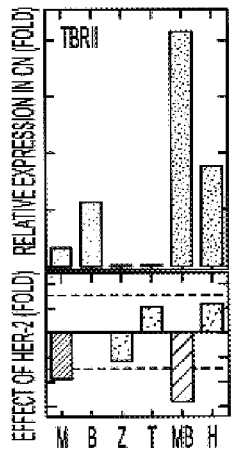 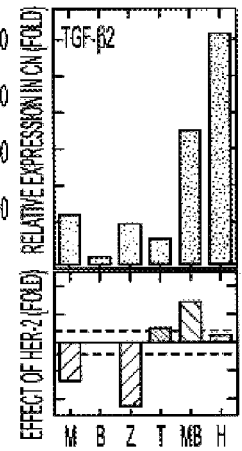 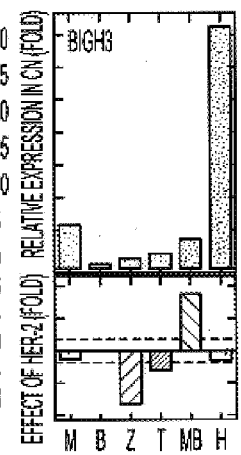 
FIG. 2B-1   FIG. 2B-2   FIG. 2B-3   FIG. 2B-4
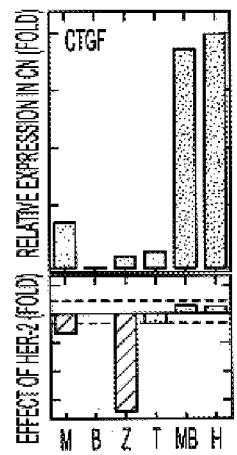  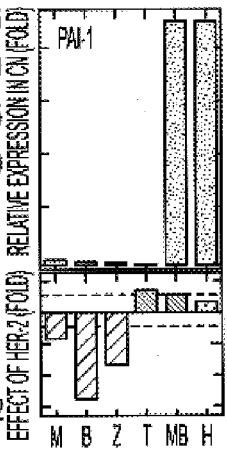 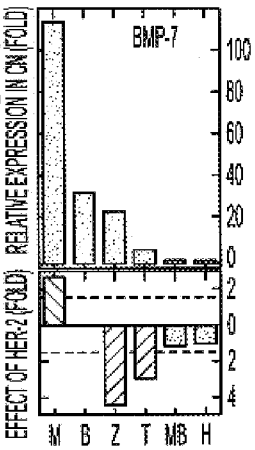
FIG. 2B-5   FIG. 2B-6   FIG. 2B-7   FIG. 2B-8

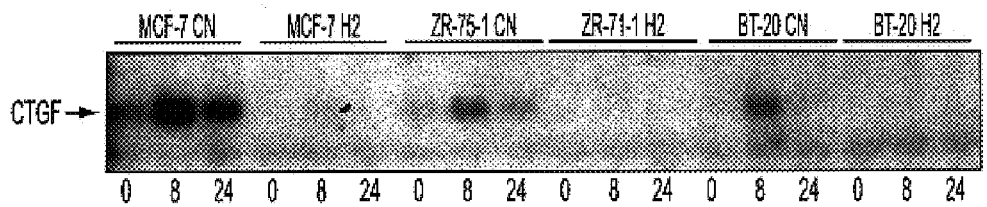
FIG. 5A
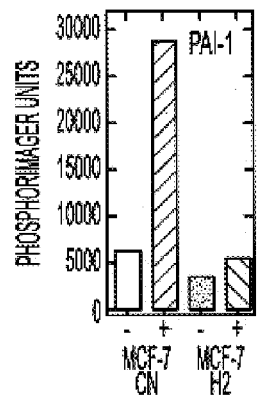 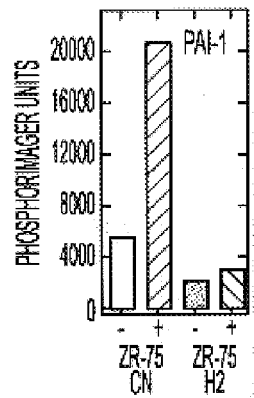 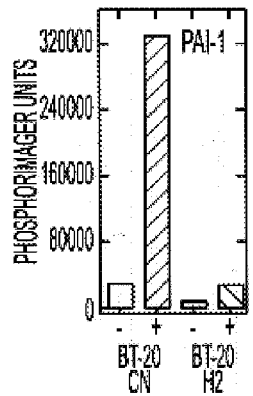
FIG. 5B-1　　FIG. 5B-2　　FIG. 5B-3
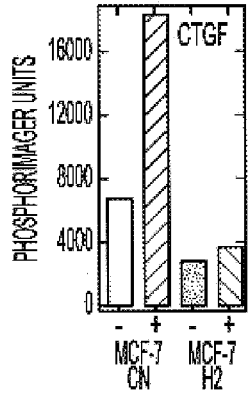 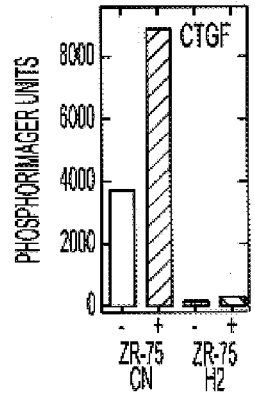 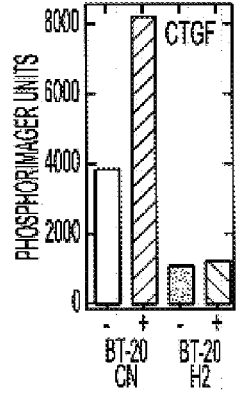
FIG. 5B-4　　FIG. 5B-5　　FIG. 5B-6
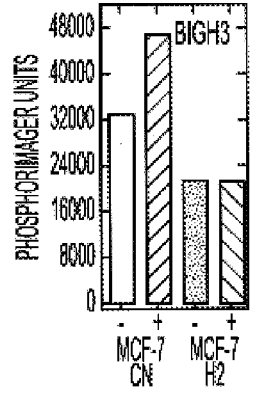 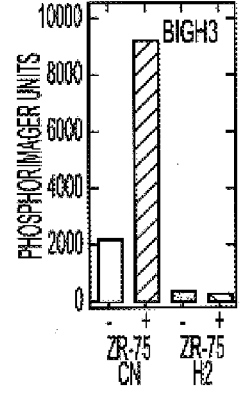 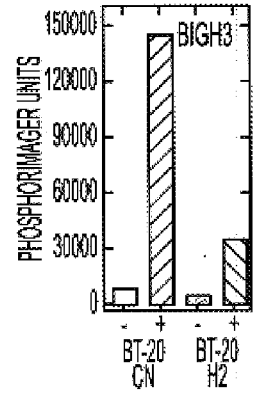
FIG. 5B-7　　FIG. 5B-8　　FIG. 5B-9

| ACCESSION # | GENE DESCRIPTION | MCF7+H FOLD | LnCAP+H FOLD | ZR75+H2 FOLD |
|---|---|---|---|---|
| 254763 | v-erb-b2 avian erythroblastic leukemia viral oncogene homolog 2 (neuro/glioblastoma derived on | 8.6 | 7.8 | 3.6 |
| AA443351.1 | v-erb-b2 avian erythroblastic leukemia viral oncogene homolog 2 (neuro/glioblastoma derived on | 8.4 | 9.3 | 3.8 |
| AA045970.1 | vascular endothelial growth factor {IMAGE:488697} | 2.1 | 2.5 | 2.5 |
| AA062961.1 | gamma-glutamyltransferase 1 {IMAGE:359931} | 2.6 | 2.2 | 3.0 |
| AA057023.1 | SH3-binding domain glutamic acid-rich protein like {IMAGE:488908} | 2.1 | 2.7 | 2.1 |
| H82136.1 | prospero-related homeobox 1 {IMAGE:220293} | 2.4 | 2.1 | 1.9 |
| N72507.1 | cytochrome P450, subfamily IIJ (arachidonic acid epoxygenase) polypeptide 2 {IMAGE:245490} | 3.4 | 1.9 | 2.0 |
| 144805 | KIAA0936 protein {IMAGE:144805} | 2.0 | 2.2 | 2.0 |
| W37595.1 | ESTs {IMAGE:321925} | 5.3 | 2.0 | 2.9 |
| 470547 | ESTs {IMAGE:470547}find genbank # | 3.8 | 2.2 | 2.1 |
| AA186508.1 | ESTs {IMAGE:624490} | 2.5 | 4.7 | 2.8 |
| AA029106.1 | ESTs {IMAGE:469999} | 2.7 | 7.1 | 3.3 |
| W21538.1 | ESTs {IMAGE:307220} | 2.9 | 9.9 | 4.9 |
| 489384 | Human insulin-like growth factor binding protein 5 (IGFBP5) mRNA {IMAGE:489384} | -1.9 | 9.8 | -12.4 |
| R36012.1 | Human insulin-like growth factor binding protein 5 (IGFBP5) mRNA {IMAGE:38481} | -2.4 | 6.5 | -23.1 |
| T65507.1 | Human insulin-like growth factor binding protein 5 (IGFBP5) mRNA {IMAGE:21542} | -2.3 | 7.3 | -22.6 |
| 486109 | v-fos FBJ murine osteosarcoma viral oncogene homolog {IMAGE:486109} | -4.1 | 2.5 | -3.9 |
| V01512 | v-fos FBJ murine osteosarcoma viral oncogene homolog {Incyte PD:341491} | -6.2 | 2.6 | -4.2 |
| 273555 | v-fos FBJ murine osteosarcoma viral oncogene homolog {IMAGE:273555} | -4.0 | 2.7 | -3.2 |
| R12840.1 | v-fos FBJ murine osteosarcoma viral oncogene homolog {IMAGE:26474} | -3.9 | 5.7 | -5.7 |
| M80583 | early growth response 1 {Incyte PD:1705208} | -2.6 | 2.8 | -3.1 |
| AF059617 | serum-inducible kinase {Incyte PD:1255087} | -1.9 | 4.4 | -2.5 |
| AA044451.1 | cysteine-rich, angiogenic inducer, 61 {IMAGE:486700} | -2.0 | 2.5 | -2.8 |
| N46210.1 | ESTs, Highly similar to CGI-131 protein [H.sapiens] {IMAGE:273558} | -2.3 | 1.9 | -2.8 |
| T83434.1 | KIAA1051 protein {IMAGE:111247} | 12.6 | -3.3 | -3.9 |
| AB028974 | KIAA1051 protein {Incyte PD:2373263} | 5.3 | -2.9 | -3.0 |
| R25594.1 | KIAA1051 protein {IMAGE:132661} | 5.8 | -2.7 | -3.2 |
| H51765.1 | KIAA1051 protein {IMAGE:193892} | 18.9 | -2.6 | -2.5 |
| T83547.1 | KIAA1051 protein {IMAGE:111113} | 12.4 | -2.6 | -2.5 |
| R00760.1 | KIAA1051 protein {IMAGE:123837} | 4.8 | -2.5 | -3.7 |
| 347518 | KIAA1051 protein {IMAGE:347518} | 10.4 | -2.0 | -2.3 |
| AA196950.1 | glyceraldehyde-3-phosphate dehydrogenase {IMAGE:629222} | 2.4 | -2.1 | -2.1 |

FIG. 7A

| | | | | |
|---|---|---|---|---|
| W47528.1 | ESTs {IMAGE:32429} | 3.4 | -2.1 | -3.1 |
| H42098.1 | ESTs {IMAGE:182426} | 2.1 | -2.1 | -2.0 |
| 471158 | CD151 antigen {IMAGE:471158} | 2.2 | -1.9 | -2.1 |
| AA135569.1 | TG-interacting factor (TALE family homeobox) {IMAGE:501393} | 1.9 | -2.3 | -1.9 |
| AA099262.1 | neuropilin 1 {IMAGE:489535} | 1.9 | -3.1 | -3.0 |
| | | | | |
| AA054712.1 | ecotropic viral integration site 1 {IMAGE:509919} | 4.8 | 2.8 | -5.7 |
| | | | | |
| N34705.1 | solute carrier family 7 (cationic amino acid transporter, y+ system), member 5 {IMAGE:268174} | 4.1 | 2.6 | -4.2 |
| AA053762.1 | solute carrier family 7 (cationic amino acid transporter, y+ system), member 5 {IMAGE:510370} | 3.6 | 2.2 | -5.2 |
| N41510.1 | solute carrier family 7 (cationic amino acid transporter, y+ system), member 5 {IMAGE:270221} | 3.9 | 2.8 | -5.2 |
| W93454.1 | solute carrier family 7 (cationic amino acid transporter, y+ system), member 5 {IMAGE:357016} | 4.6 | 2.8 | -3.1 |
| M80244 | solute carrier family 7 (cationic amino acid transporter, y+ system), member 5 {Incyte PD:191101} | 1.9 | 2.3 | -2.8 |
| | | | | |
| AA031743.1 | Homo sapiens mRNA; cDNA DKFZp564A072 (from clone DKFZp564A072) {IMAGE:470501} | 2.5 | 2.2 | -2.6 |
| AA045870.1 | Homo sapiens mRNA; cDNA DKFZp564A072 (from clone DKFZp564A072) {IMAGE:488622} | 2.6 | 2.3 | -2.4 |
| | | | | |
| AA040660.1 | spermidine/spermine N1-acetyltransferase {IMAGE:487351} | 2.7 | 2.1 | -3.2 |
| 530860 | 3-hydroxy-3-methylglutaryl-Coenzyme A synthase 1 (soluble) {IMAGE:530860} | 3.8 | 2.4 | -2.6 |
| W78844.1 | squalene epoxidase {IMAGE:415621} | 2.3 | 2.6 | -2.1 |
| AA046763.1 | alpha-1-antichymotrypsin {IMAGE:488360} | 8.1 | 2.2 | -2.0 |
| H73130.1 | B-cell CLL/lymphoma 2 {IMAGE:232714} | 2.4 | 2.0 | -3.3 |
| AA279509.1 | ESTs, Weakly similar to R31665_2 [H.sapiens] {IMAGE:704512} | 3.2 | 2.0 | -2.0 |
| N36526.1 | dihydropyrimidinase-like 2 {IMAGE:268518} | 2.4 | 2.0 | -2.0 |
| W92498.1 | amyloid beta (A4) precursor protein-binding, family B, member 2 (Fe65-like) {IMAGE:361815} | 2.1 | 1.9 | -2.1 |
| | | | | |
| 90434 | REMOVED_FROM_DATABASE {Incyte PD:90434} | 2.6 | -2.1 | 2.2 |
| | | | | |
| U89606 | pyridoxal (pyridoxine, vitamin B6) kinase {Incyte PD:1749883} | -2.3 | -2.0 | -2.0 |

FIG. 7B

HER-2/NEU OVEREXPRESSION ABROGATES GROWTH INHIBITORY PATHWAYS

CROSS REFERENCE TO RELATED APPLICATIONS

This application is a non-provisional application claiming priority under Section 119(e) to provisional application Ser. No. 60/190,598, filed Mar. 20, 2000, the contents of which are incorporated herein by reference.

FIELD OF THE INVENTION

The invention described herein relates to diagnostic and therapeutic methods targeting cell signaling pathways perturbed in syndromes involving disregulated cellular proliferation.

BACKGROUND OF THE INVENTION

Cancers are the second most prevalent cause of death in the United States, causing 450,000 deaths per year. One in three Americans will develop cancer, and one in five will die of cancer. While substantial progress has been made in identifying some of the likely environmental and hereditary causes of cancer, there is a need for additional diagnostic and therapeutic modalities that target cancer and related diseases and disorders.

A number of so-called cancer genes, i.e., genes that have been implicated in the etiology of cancer, have been identified in connection with hereditary forms of cancer and in a large number of well-studied tumor cells. Cancer genes ate broadly classified into "oncogenes" which, when activated, promote tumorigenesis, and "tumor suppressor genes" which, when damaged, fail to suppress tumorigenesis. While these classifications provide a useful method for conceptualizing tumorigenesis, it is also possible that a particular gene may play differing roles depending upon the particular allelic form of that gene, its regulatory elements, the genetic background and the tissue environment in which it is operating.

The HER-2/neu is an illustrative oncogene that is member of the tyrosine protein kinase family of oncogenes and shares a high degree of homology with the epidermal growth factor receptor and presumably plays a role in cell growth and/or differentiation. Amplification and/or overexpression of the HER-2/neu type I receptor tyrosine kinase has been detected in 25–30% of human breast cancers. This alteration is an independent prognostic factor predicting poor clinical outcome. HER-2/neu overexpression in experimental models has been associated with an aggressive phenotype, including increased proliferation rate, DNA synthesis, anchorage-independent growth, tumorigenicity and metastatic potential. Recently, this genetic alteration has been successfully targeted in humans using the monoclonal antibody HERCEPTIN. Despite these advances, the molecular pathways leading from HER-2/neu overexpression to increased malignancy remain unclear and few targets downstream of HER-2/neu have been identified. Much remains to be learned about how HERCEPTIN functions as an anti-tumor agent and why certain HER-2/neu overexposing tumors respond to therapy while many others do not.

Ligands of the TGF-β receptor (TGF-β1, TGF-β2 and TGF-β3) are also known to play a role in syndromes involving the disregulation of cellular growth. Specifically, TGF-β ligands are involved in the growth inhibition in a number of cell types, and loss of this negative regulation is thought to contribute to tumor development. Studies have demonstrated that TGF-β ligands suppress the growth of certain cancer cell lines, that antisense inhibition of TGF-β enhances the tumorigenicity of weakly tumorigenic cancer cell lines, and that certain tumor cells are unresponsive to growth inhibition by TGF-β ligands.

While researchers have identified a variety of genes involved in growth disregulation such as Her-2/neu and TGF-β, there is need for more detailed analyses of the genetic profiles exhibited by cells in which the regulatory processes that control cell growth have been disrupted. Moreover, an understanding of how the products of genes involved in disregulated cell growth interact in a larger context is needed for the development of improved diagnostic and therapeutic methods for identifying and treating pathological syndromes associated with growth disregulation such as cancer.

SUMMARY OF THE INVENTION

The present invention provides methods for obtaining genetic profiles of cancer cells in order to assess the status of a cancer in an individual. In addition, the present invention provides methods for inhibiting the growth of cancer cells that exhibit certain genetic profiles. These methods identify an important link between HER-2/neu overexpression and loss of growth inhibition by the TGF-β signaling pathway in cancer cells.

The invention disclosed herein provides a number of embodiments pertaining to the analysis of gene expression of mammalian cells. In these methods, the mRNA expression of a plurality of genes is examined in order to gain information that is useful in the diagnosis and/or prognosis of a pathological condition such as cancer. A typical embodiment consists of a method of examining a breast cell for evidence of a malignant phenotype by examining the mRNA expression profile of at least two mRNA polynucleotides in the cell, wherein the mRNA polynucleotides are selected from a first group of mRNA polynucleotides that are overexpressed in cells that overexpress Her-2/neu and a second group of mRNA polynucleotides that are underexpressed in cells that overexpress Her-2/neu. An mRNA expression profile in which the mRNA levels of the mRNA polynucleotides in the first group are increased greater than about 2 fold relative to the corresponding mRNA levels of the mRNA polynucleotides in normal breast cells and the mRNA levels of the mRNA polynucleotides in the second group are decreased greater than about 2 fold relative to the corresponding mRNA levels of the mRNA polynucleotides in normal breast cells is indicative of a malignant phenotype.

In preferred embodiments of the invention, the mRNA expression profile of at least one mRNA polynucleotide from the first group is examined and the mRNA expression profile of at least one mRNA polynucleotide from the second group is examined. In highly preferred embodiments, the mRNA expression profile of at least 3, 4, 5, 6, 7, 8, 9, 10 or all of the mRNA polynucleotides is examined. While the mRNA expression profile of genes can be evaluated by a wide variety of methods known in the art, in preferred embodiments, the mRNA expression profile is examined using a cDNA microarray.

Another related embodiments of the invention that pertains to the analysis of gene expression consists of a method for examining a breast cell for evidence of a malignant phenotype by comparing the level of mRNA expression of bone morphogenetic protein 7 (BMP-7) with the level of mRNA of at least one comparative gene, wherein an mRNA expression profile in which levels of BMP-7 mRNA are lower than those of the comparative gene is indicative of a malignant phenotype. In preferred embodiments of the invention, the level of BMP-7 mRNA expression is compared to 2, 3, 4, 5, 6, 7 or 8 comparative genes is examined. In a further embodiment of the invention, the cytological characteristics of the cell are examined, preferably for mesenchymal characteristics and/or epithelial characteristics.

Building upon the data generated in the profiling experiments, subsequent experiments revealed that an antibody capable of inhibiting Her-2/neu receptor function and a TGF-β family member can act synergistically to inhibit the growth of mammalian cells, particularly mammalian cancer cells. The invention provides various methods that involve the use of an antibody capable of inhibiting Her-2/neu receptor function and a TGF-β family member for inhibiting the growth of mammalian cells. For example, the invention provides a method for inhibiting the growth of mammalian cells comprising exposing a mammalian cell, such as a cancer cell (preferably a breast or ovarian cancer cell), to an antibody capable of inhibiting Her-2/neu receptor function and a TGF-β family member in an amount effective to synergistically inhibit cell growth. The cell may be in cell culture or in a mammal, e.g. a mammal suffering from cancer or a condition in which inhibiting the growth of the cells is desirable. Thus, the invention includes a method for treating a mammal suffering from cancer comprising administering an effective amount of an antibody capable of inhibiting Her-2/neu receptor function and a TGF-β family member, as disclosed herein.

The invention also provides compositions which comprise an antibody capable of inhibiting Her-2/neu receptor function and/or a TGF-β family member. Optionally, the compositions of the invention will include pharmaceutically acceptable carriers or diluents. Preferably, the compositions will include an antibody capable of inhibiting Her-2/neu receptor function and/or a TGF-β family member in an amount which is effective to synergistically inhibit the growth of mammalian cells.

The invention also provides articles of manufacture and kits which include reagents for analyzing the expression of genes within a cell, an antibody capable of inhibiting Her-2/neu receptor function and/or a TGF-β family member.

BRIEF DESCRIPTION OF THE DRAWINGS

FIGS. 2A–2B. Expression of TGF-β pathway related genes in control and HER-2/neu overexpressing breast cancer cells. a Relative expression of HER-2/neu in engineered breast cancer cells. The Northern blot analysis of HER-2/neu message in control (CN) and HER-2 (H2) cell lines is shown to the left. The double asterisk (**) indicates the position of the message of HER-2/neu fused to the neomycin resistance gene and the single asterisks (*) indicates the position of the endogenous HER-2/neu transcript. The numbers to the right represent the fold increase in the H2 cells compared to CN as determined by phosphorimager quantitation. b Relative expression of TGF-β pathway genes among breast cancer cell lines and the effect of HER-2 on these levels. The upper panels of each graph show the relative expression levels for each of the indicated genes obtained by phosphorimager quantitation of Northern blots. The numbers on the y-axis represent relative signal obtained by setting the value of the cell line with the lowest signal to 1. The abbreviations used for the cell lines on the x-axis are defined in a. The lower panels of each graph show the effect of HER-2 on the expression of each gene represented as fold difference in expression between CN and H2 cells. Bars above the origin (solid line) show values as H2/CN (i.e. upregulated by HER-2) and bars below represent values as CN/H2 (i.e. downregulated by HER-2). Values less than 1.5 fold (marked by dashed line) were not considered to be significant and are shaded gray. Values between 1.5 and 2.0 fold are hatched and values >2.0 fold are solid.

FIGS. 5A–5D. HER-2/neu overexpression inhibits TGF-β1 induction of downstream target genes. a Northern analysis of CTGF expression. Coding sequence of CTGF was $^{32}$P-labeled and used to probe a filter containing 8 ug of total RNA/lane isolated from the indicated cell lines. Cells were treated in T225 flasks with either diluent or 2 ng/ml of TGF-β1 for 8 or 24 hr. b Quantitative representation of Northern analysis of PAI-1, CTGF and BIGH3. Northern blots were generated using $^{32}$P-labeled coding sequence probes as in a and the signals were measured on a phosphorimager. The relative expression of each gene in the absence ((−); solid bats) or presence ((+); hatched bats) of TGF-β1 treatment is shown for each cell line. The (+) signals for PAT-1 and BIGH3 are the 24 hr time points whereas the 8 hr time point is shown for CTGF. Black and gray bats represent CN and H2 cell lines respectively. c HER-2 overexpression abrogates induction of the cdk4 inhibitor p15$^{INK4B}$ by TGF-β1. Western blot analysis of total cellular extracts from cells treated for the indicated times with diluent control (0 hr) or 2 ng/ml of TGF-β1. The black arrows mark the position of the p15$^{INK4B}$ protein doublet detected with the polyclonal anti-p15 antibody (Santa Cruz Biotechnologies). The bottom panels show autoradiograms of the same membranes after stripping and reprobing with a polyclonal antibody to cdk4 (Santa Cruz). d Overexpression of HER-2 causes global inhibition of TGF-β inducible genes. Gem V of the cDNA arrays was used to profile transcriptional changes in MCF-7/CN and MCF-7/H2 cells induced by a 24 hr treatment of 2 ng/ml of TGF-β1 compared to control treated cells. The data is displayed as element number (1-9242) on the x-axis vs. relative fold change between TGF-β-1 and control treated RNA. Negative ratio's represent TGF-β1 activated genes (i.e. the signal from the TGF-β1 RNA was greater than the diluent signal) and the positive ratios represent TGF-β1 repressed signals.

FIGS. 7A–B. Comparative table showing information on genes that exhibit altered expressed in multiple cell lines (MCF7, LnCAP and IZR75 transfected with HER2).

DETAILED DESCRIPTION OF THE INVENTION

I. Definitions

Figure 1:
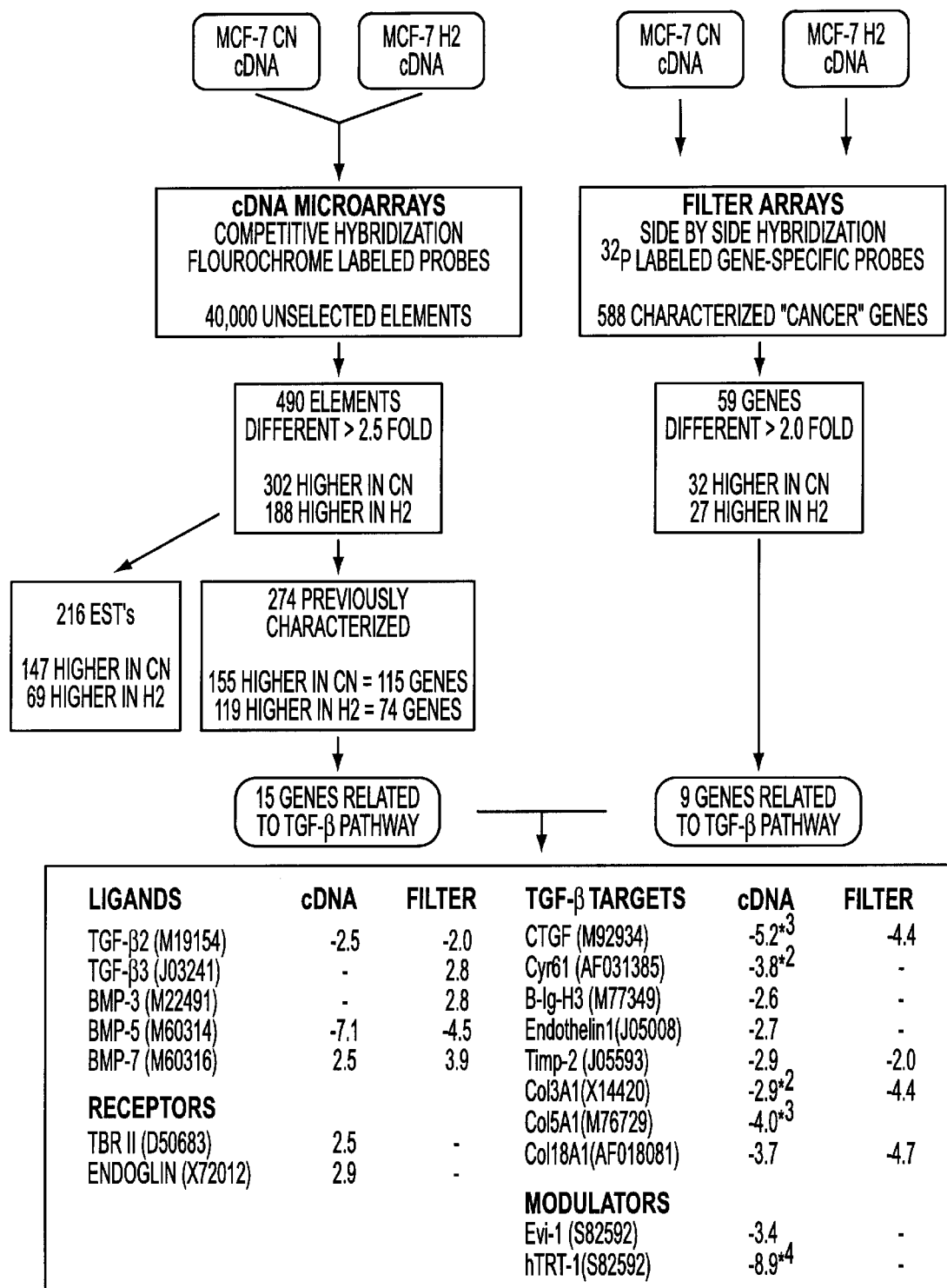
FIG. 1. Transcript profiling of HER-2/neu overexpressing MCF-7 breast cancer cells reveals altered expression of genes in the TGF-β pathway. Schematic summary and comparison of the results obtained using cDNA microarrays (Synteni/Incyte) on the left half and filter blots (Atlas Cancer Blot, Clontech) on the right. Changes in 274 of the elements occurred in a total of 189 individual, previously described genes whose full-length sequence is available in GenBank. The remaining changes (216 elements) occurred in EST sequences or in genes from sequencing projects with no additional published information. The magnitudes of the relative expression differences were between 2.5 and 6 fold for the majority of the elements (93%), however, there were differential hybridization signals up to 21 fold. The results of the filter array on the right represent spots having 2 fold or greater differences between MCF/CN and MCF/H2 in both of the duplicate experiment described in methods. A total of 15 genes from the cDNA arrays and 9 from the filter arrays (most of which were overlapping) were predicted to have functions relating to the TGF-β1 pathway based on the literature and are listed by name and GenBank number in the box. Whole number values signifies expression changes that were higher in the MCF-7 HER-2 cells (H2) (i.e. "upregulated by HER-2). Negative numbers signify that the signal was higher in the MCF-7 control cells (CN) (i.e. "downregulated" by HER-2). Values are listed as fold difference and the asterisks indicate that differential hybridization at more than one element was detected. The number after the asterisks is the number of independent elements that were averaged to give the final fold change.

"Growth inhibition" when used herein refers to the growth inhibition of a cell in vitro and/or in vivo. The inhibition of cell growth can be measured by a wide variety of methods known in the art including those described in Example 3 below. A "growth inhibitory agent" when used herein refers to a compound or composition which inhibits growth of a cell in vitro and/or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13.

"Biologically active" or "biological activity" for the purposes herein means (a) having the ability to inhibit the growth of at least one type of mammalian cancer cell or experimentally transformed cell in vivo or ex vivo; (b) capable of raising an antibody, i.e., immunogenic; or (c) retaining the activity of a native or naturally-occurring antibody capable of inhibiting Her-2/neu receptor function.

As used herein, the term "synergy" or "synergism" or "synergistically" refers to the interaction of two or more agents so that their combined effect is greater than the sum of their individual effects.

The term "antibody" when used for example in reference to an "antibody capable of inhibiting Her-2/neu receptor function" is used in the broadest sense and specifically covers intact monoclonal antibodies, polyclonal antibodies, multispecific antibodies (e.g. bispecific antibodies) formed from at least two intact antibodies, and antibody fragments so long as they mimic the inhibitory activity of an antibody capable of inhibiting Her-2/neu receptor function.

"Antibody fragments" comprise a portion of an intact antibody, generally the antigen binding or variable region of the intact antibody. Examples of antibody fragments include Fab, Fab', F(ab')2, and Fv fragments, diabodies, single chain antibody molecules, and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature*, 352:624–628 (1991) and Marks et al. *J. Mol. Biol.*, 222:581–597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851–6855 (1984)).

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementarity-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., *Nature*, 321:522–525 (1986); Reichmann et al., *Nature* 332:323–329 (1988); and Presta, *Curr. Op. Struct. Biol.*, 2:593–596 (1992). The humanized antibody includes a PRIMATIZED™ antibody wherein the antigen-binding region of the antibody is derived from an antibody produced by immunizing macaque monkeys with the antigen of interest.

The monoclonal antibodies herein include chimeric, hybrid and recombinant antibodies produced by splicing a variable (including hypervariable) domain of an anti-Her-2/neu receptor antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity or properties. See, e.g. U.S. Pat. No. 4,816,567 and Mage et al., in *Monoclonal Antibody Production Techniques and Applications*, pp.79–97 (Marcel Dekker, Inc.: New York, 1987).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art. In one embodiment, the human antibody is selected from a phage library, where that phage library expresses human antibodies (Vaughan et al. *Nature Biotechnology*, 14:309–314 (1996): Sheets et al. *PNAS*, (USA) 95:6157–6162 (1998)); Hoogenboom and Winter, *J. Mol. Biol.*, 227:381 (1991); Marks et al., *J. Mol. Biol.*, 222:581 (1991)). Human antibodies can also be made by introducing human immunoglobulin loci into transgenic animals, e.g., mice in which the endogenous immunoglobulin genes have been partially or completely inactivated.

Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al, *Bio/Technology*, 10: 779–783 (1992); Lonberg et al., *Nature,* 368: 856–859 (1994); Morrison, *Nature,* 368:812–13 (1994); Fishwild et al., *Nature Biotechnology,* 14: 845–51 (1996); Neuberger, *Nature Biotechnology.* 14: 826 (1996); Lonberg and Huszar, *Intern. Rev. Immunol.,* 13:65–93 (1995). Alternatively, the human antibody may be prepared via immortalization of human B lymphocytes producing an antibody directed against a target antigen (such B lymphocytes may be recovered from an individual or may have been immunized in vitro). See, e.g., Cole et al., *Monoclonal Antibodies and Cancer Therapy,* Alan R. Liss, p. 77 (1985); Boerner et al., *J. Immunol.,* 147 (1):86–95 (1991); and U.S. Pat. No. 5,750,373.

An "affinity matured" antibody is one with one or more alterations in one or more CDRs thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology,* 10:779–783 (1992) describes affinity maturation by VH and VL domain shuffling. Random mutagenesis of CDR and/or framework residues is described by: Barbas et al. *Proc Nat. Acad. Sci,* USA 91:3809–3813 (1994); Schier et al. *Gene,* 169:147–155 (1995); Yelton et al *J. Immunol.,* 155:1994–2004 (1995); Jackson et al., *J. Immnunol.,* 154(7):3310–9 (1995); and Hawkins et al, *J. Mol. Biol.,* 226:889–896 (1992).

The terms "agonist" and "agonistic" when used herein refer to a molecule which is capable of, directly or indirectly, substantially inducing, promoting or enhancing biological activity or activation of a molecule such as a TGF-β family member. Preferably, the agonist is a molecule which is capable of inhibiting the growth of a mammalian cell.

"Isolated," when used to describe the various proteins disclosed herein, means protein that has been identified and separated and/or recovered from a component of its natural environment. Contaminant components of its natural environment are materials that would typically interfere with diagnostic or therapeutic uses for the protein, and may include enzymes, hormones, and other proteinaceous or non-proteinaceous solutes. In preferred embodiments, the protein will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated protein includes protein in situ within recombinant cells, since at least one component of the protein natural environment will not be present. Ordinarily, however, isolated protein will be prepared by at least one purification step.

The term "prodrug" as used in this application refers to a precursor or derivative form of a pharmaceutically active substance that is less cytotoxic to cancer cells compared to the parent drug and is capable of being enzymatically activated or converted into the more active parent form. See, e.g., Wilman, "Prodrugs in Cancer Chemotherapy" *Biochemical Society Transactions,* 14, pp. 375–382, 615th Meeting Belfast (1986) and Stella et al., "Prodrugs: A Chemical Approach to Targeted Drug Delivery," *Directed Drug Deliver,* Borchardt et al., (ed.), pp. 247–267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described below.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of conditions like cancer. Examples of chemotherapeutic agents include alkylating agents alkyl sulfonates such as busulfan; aziridines such as benzodopa, anti-metabolites such as methotrexate; folic acid analogues such as denopterin; taxoids, e.g. paclitaxel TAXOL®, Bristol-Myers Squibb Oncology, Princeton, N.J.) and doxetaxel (TAXOTERE®, Rhône-Poulenc Rorer, Antony, France); platinum analogs such as cisplatin; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

The term "cytokine" is a genetic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-alpha; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta and -gamma colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; a tumor necrosis factor such as TNF-alpha or TNFbeta; and other polypeptide factors including LIF and kit ligand (KL). As used herein, the term cytokine includes proteins from natural sources or from recombinant cell culture and biologically active equivalents of the native sequence cytokines.

"Treatment" or "therapy" refer to both therapeutic treatment and prophylactic or preventative measures.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing tumor burden or volume, the time to disease progression (TTP) and/or determining the response rates (RR).

"Mammal" for purposes of treatment or therapy refers to any animal classified as a mammal, including humans, domestic and farm animals, and zoo, sports, or pet animals, such as dogs, horses, cats, cows, etc. Preferably, the mammal is human.

The terms "cancer", "cancerous", or "malignant" refer to or describe the physiological condition in mammals that is typically characterized by unregulated cell growth. Examples of cancer include but ate not limited to, carcinoma, lymphoma, blastoma, sarcoma, and leukemia. More particular examples of such cancers include breast cancer, ovarian cancer, colon cancer, colorectal cancer, rectal cancer, squamous cell cancer, small-cell lung cancer, non-small cell lung cancer, Hodgkin's and non-Hodgkin's lymphoma, testicular cancer, esophageal cancer, gastrointestinal cancer, renal cancer, pancreatic cancer, glioblastoma, cervical cancer, glioma, liver cancer, bladder cancer, hepatoma, endometrial carcinoma, salivary gland carcinoma, kidney cancer, liver cancer, prostate cancer, vulval cancer, thyroid cancer, hepatic carcinoma and various types of head and neck cancer.

As used herein, the term "polynucleotide" means a polymeric form of nucleotides of at least 10 bases or base pairs in length, either ribonucleotides or deoxynucleotides or a modified form of either type of nucleotide, and is meant to include single and double stranded forms of DNA and/or RNA.

As used herein, the terms "hybridize", "hybridizing", "hybridizes" and the like, used in the context of polynucleotides, are meant to refer to conventional hybridization conditions, preferably such as hybridization in 50% formamide/6×SSC/0.1% SDS/100 µg/ml ssDNA, in which temperatures for hybridization are above 37 degrees C. and temperatures for washing in 0.1×SSC/0.1% SDS are above 55 degrees C.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, are identified by but not limited to those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium. citrate), 50 mM sodium phosphate (PH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium. citrate) and 50% formamide at 55° C., followed by a high-stringency wash consisting of 0.1×SSC containing EDTA at 55° C.

II. Characterization of the Invention

Amplification/overexpression of non-mutated HER-2/neu is detected in 25–30% of human breast cancers and is independently predictive of aggressive disease behavior and poor clinical outcome. Breast cancer patients that overexpress HER-2/neu are less likely to respond to anti-estrogen treatment as well as chemotherapy. A ligand that binds directly to HER-2/neu has not yet been identified, and it now seems clear that HER-2/neu serves as a co-receptor that facilitates ligand binding and activation of EGFR, HER-3 and HER-4. Recently, the monoclonal antibody HERCEPTIN, directed at the HER-2/neu extracellular domain and capable of inhibiting Her-2/neu receptor function, has shown activity as a single agent in about 21% of women with HER-2/neu positive metastatic breast cancer. Moreover, the antitumor responses with HERCEPTIN in combination with chemotherapy exceeded either therapeutic modality alone.

The molecular and cellular mechanisms responsible for the clinical success of HERCEPTIN are the focus of intense investigation. It has been suggested that anti-receptor antibodies may work by one or more distinct mechanisms, including blockade of ligand binding, disruption of constitutive activation, induction of an antibody-specific signal, enhancement of antibody-dependant or cell-mediated cytotoxicity and downregulation of receptor density and several of these mechanisms may be relevant to HERCEPTIN. The short term effects of HERCEPTIN appear to be cytostatic rather that cytotoxic which provides evidence that once tumor growth is slowed, endogenous growth inhibitors in the microenvironment may play a role in controlling growth. Experimentally, many phenotypic changes associated with HER-2/neu overexpression have been identified that are consistent with an aggressive clinical phenotype (i.e. increased growth in vitro, increased tumorigenicity in vivo and increased metastatic potential in orthotopic implantation models. HER-2/neu overexpression in tumor cell lines results in constitutive elevation of HER-2/neu phosphorylation and alterations in ligand-dependent transphosphorylation of the HER co-receptors.

In order to elucidate the molecular pathways downstream of HER-2/neu, a comprehensive gene expression analysis or "profile" of human breast cancer cells engineered to overexpress HER-2/neu is described. Transcript profiling experiments disclosed herein reveal that HER-2/neu overexpression results in characteristic patterns of gene expression that are associated with this malignant phenotype. These include alterations in the TGF-$\beta$ pathway, findings that are consistent with the reduced responsiveness to TGF-$\beta$ that is observed in such cells.

The profiling patterns disclosed herein are useful for assessing the malignant phenotype of cells. For example, as discussed above, the profiling patterns obtained from malignant cells showed the presence of alterations in TGF-$\beta$ pathways. This phenotype is confirmed by subsequent data showing that cells engineered to overexpress HER-2/neu exhibit resistance to TGF-$\beta$1 mediated growth inhibition. In addition, activation of the TGF-$\beta$ transcriptional program is globally inhibited by HER-2/neu overexpression. Furthermore several "natural" HER-2 overexpressing cell lines, (i.e. cells isolated from breast cancers containing the HER-2/neu amplicon) are resistant to growth inhibition by TGF-$\beta$1.

Surprisingly, we discovered that by treating these TGF-$\beta$ resistant cells with HERCEPTIN (an antibody capable of inhibiting Her-2/neu receptor function), one can re-sensitize these cells to the effects of TGF-$\beta$1. These findings provide evidence that the greater proliferation rates of HER-2/neu overexpressing cells observed in vitro and in vivo are linked to TGF-$\beta$ resistance, and that reversal of this phenomenon may contribute to the antitumor activity of HERCEPTIN. Moreover, the finding that a combination of an antibody capable of inhibiting Her-2/neu receptor function and a TGF-$\beta$ family member synergistically inhibit the growth of mammalian cells provides new therapeutic options for the treatment of cancers that overexpress Her-2/neu.

III. Methods and Materials

A. Methods for Profiling Gene Expression in Mammalian Cancer Cells

The profiling methods described herein are used to examine alterations in gene expression associated with pathological syndromes such as cancer. For example, information obtained from the examination of profile alterations in gene expression that occur in breast cancer cells in response HER-2/neu overexpression provides information on the linkage between poor prognosis and amplification of this receptor in human tumors. As discussed in the examples below, in order to evaluate the status of a typical model of breast cancer, breast cancer cells and cell lines engineered to overexpress HER-2/neu were examined. In particular, for each HER-2/neu (H2) transfected line, a control cell line (CN) containing the empty neomycin vector was also selected and cultured in parallel. Among these cell lines, MCF-7/CN and MCF-7/H2 cells were used for the cDNA microarray experiments. The expression profile of MCF-7/H2 cells was compared to that of MCF-7/CN cells using both microarrays and filterarrays. Using the microarrays, approximately 490 elements were scored as showing differences of greater than 2.5 fold in hybridization signals in MCF-7/H2 compared to MCF-7/CN cDNA. The filterarray experiments yielded 59 differentially expressed genes 21 of which were also found to be differentially expressed using the microarrays.

In the profiles generated herein, several TGF-$\beta$ superfamily ligands and receptors showed significantly altered expression in the MCF-7/H2 cells (see, e.g. FIG. 1). Specifically, differential expression of 5 TGF-$\beta$ ligands (TGF-$\beta$2, TGF-$\beta$3, BMP-3, BMP-5 and BMP-7) and 2 receptors, the TGF-$\beta$ type II receptor (TBRII) (Lin et al., Cell 68, 775–85 (1992); Lin et al., Mol Reprod Dev 32, 105–10 (1992) and Massague, J. Cell 69, 1067–70 (1992) and the type III receptor (endoglin) (Yamashita, H., et al. J Biol Chem 269, 1995–2001 (1994); Letamendia, A., et al. J Biol Chem 273, 33011–9 (1998) and Barbara et al.,. J Biol Chem 274, 584–94 (1999)) was detected. The consistent suppression of TGF-$\beta$ activated genes (CTGF, Cyr61, B-Ig-H3, Endothelin 1, Timp-2, Col3A1, Col5A1, Col8A1 etc) in response to HER-2/neu overexpression provided strong evidence that TGF-$\beta$ signaling is inhibited in MCF-7/H2 cells (see, e.g. FIG. 1). In addition, the overall expression pattern of a subset of genes in the CN cell lines appears to delineate two distinct types with respect to the TGF-$\beta$ pathway, with the characteristics exhibited by these two distinct types having specific clinical implications. The first, (Type A), was characterized by low level expression of the TGF-$\beta$ receptor (TBRII) and the TGF-$\beta$2 ligand, moderate to low expression of the downstream target genes BIGH3, CTGF, Cyr61, PAI-1 and TIMP-2, and relatively high expression of BMP-7. The control cell lines that displayed the Type A profile are MCF-7/CN, BT-20/CN, ZR-75-1/CN, and T47D/CN. The cells displaying the second profile (Type B), which is essentially the opposite of the type A profile, includes the MDA-MB-231/CN and HBL-100/CN. These cells were found to overexpress TBRII and the TGF-$\beta$2 ligand, as well as downstream target genes (BIGH3, TIMP-2, CTGF, Cyr61 and PAI-1) while BMP-7 was essentially undetectable.

The distinction between the two transcriptional profiles correlates with phenotypic differences associated with the malignancy of cancer cells. In particular, the Type A cells tend to retain epithelial characteristics, generally growing in clumps of cobblestone shaped cells whereas the Type B cells are more mesenchymal (i.e. elongated, motile individual cells). In this context, carcinoma cell exhibiting a mesenchymal-like phenotype (as seen in Type B) are known to exhibit dramatically increased motility, invasiveness and metastatic potential in in vitro and in vivo cancer models (see, e.g. Bae et al., Breast Cancer Res. Treat. 24(3): 241–255 (1993)). Moreover, TGF-$\beta$ is shown to be a critical mediator of the epithelial to mesenchymal transition (EMT) described in progression of several epithelial cancer models (Peik E et al, J. Cell Sci. 112(Pt 24): 4557–68 (1999). Consequently, these results provide evidence that TGF-$\beta$ transcriptional programs are altered in a relatively consistent manner in response to HER-2/neu overexpression in breast tumor cell-lines and that the profiles disclosed herein can be correlated with malignant phenotypes. This is especially true for cells that express low levels of TGF-$\beta$ ligands/receptors (Type A) versus cells that appear to be vigorously stimulated by autocrine signaling due to TGF-$\beta$ ligand/receptor overexpression (Type B).

As disclosed above, cDNA arrays are useful for globally examining changes in gene expression profiles in HER-2/neu overexpressing cells. Using the information obtained from these profiles group of these genes, physiological models (e.g. pathways altered upon HER-2/neu overexpression) can then be generated and directly tested. For example, the microarray analysis provided evidence that TGF-$\beta$1 pathways were perturbed in cells that over express Her-2/neu. Using this observation, cells engineered to overexpress HER-2/neu were then evaluated to determine whether they had altered biological responses to TGF-$\beta$1. Once it was determined that such cells had altered biological responses to TGF-$\beta$1, this information was then used to show that treatment with an anti-HER-2 monoclonal antibody sensitizes cells to TGF-$\beta$1, a finding which corroborates the original microarray data suggesting that the lack of growth response in these cells is due to signals emanating from HER-2/neu. The previously unreported connection between HER-2/neu signaling and TGF-β resistance based on these profiling experiments and the subsequent validation using cell line models, establishes the power that this approach has for obtaining insights into oncogenic processes such as HER-2/neu mediated tumorigenesis.

The invention disclosed herein has a number of embodiments pertaining to the analysis of gene expression of mammalian cells. In these methods, the mRNA expression of a plurality of genes is examined in order to gain information that is useful in the diagnosis or prognosis of a pathological condition such as cancer. An illustrative embodiment of the invention consists of a method for identifying cells having an altered responsiveness to a Transforming Growth Factor-β family member selected from the group consisting of Transforming Growth Factor-β1 (TGF-β1), Transforming Growth Factor-β2 TGF-β2) and Transforming Growth Factor-β3 (TGF-β3) comprising examining the expression of Her-2/neu in the cells, wherein the overexpression of Her-2/neu in the cells provides evidence of an altered responsiveness to a Transforming Growth Factor-β family member.

The methods disclosed herein are useful for examining cells that may exhibit a malignant phenotype. In particular, oncogenesis is known to be a multistep process where cellular growth becomes progressively disregulated and cells progress from a normal phenotype to a malignant one (see, e.g., Alers et al., Lab Invest. 77(5): 437–438 (1997) and Isaacs et al., Cancer Surv. 23: 19–32 (1995)). In this context, skilled artisans endeavor to identify cells having a malignant phenotype (also described as the oncogenic, tumorigenic or transformed phenotype) in order diagnose cancers and to obtain information useful for the prognosis of these pathologies. Cells characterized as having a malignant phenotype exhibit a number of characteristics including altered gene expression, morphological changes, resistance to chemotherapeutics such as tamoxifen and increased proliferation and motility (see. e.g. Chazin et al., Oncogene 7(9): 1859–1866 (1992); Oh et al., N.A.R. 27(20): 4008–4017 (1999); Lonn et al., Clin. Cancer Res. 1(10): 1189–1194 (1995) and Karni et al., Oncogene 18(33): 4654–4662 (1999)). While a wide variety of factors associated with malignancy are used to identify a malignant phenotype including the expression of genes associated with malignancy (e.g. PSA, PSCA and PSM expression etc.) and gross cytological observations (see, e.g., Bocking et al., 1984, Anal. Quant. Cytol. 6(2):74–88; Eptsein, 1995, Hum. Pathol. 26(2):223–9; Thorson et al., 1998, Mod. Pathol. 11(6):543–51; Baisden et al. 1999, Am. J. Surg. Pathol. 23(8):918–24), additional methods are needed to facilitate the diagnosis and therapy of various cancers such as breast cancer. For example, by examining a biological sample for early evidence of a malignant phenotype the early detection of a pathology such as cancer can be identified before the disease has progressed to a stage at which therapeutic options are more limited.

A representative embodiment of the invention includes methods involving the characterization of a Her-2 responsive gene set in a cell having a malignant phenotype for example to stratify Her-2 positive breast cancer patients with respect to prognosis, HERCEPTIN efficacy, response to chemotherapy, and the response to hormone therapy. In this context, the status of Her-2/neu expression and TGF-β sensitivity (and/or a Her-2 responsive gene set) may provide information useful for predicting a variety of factors including susceptibility to advanced stage disease, rate of progression, and/or tumor aggressiveness. Another typical embodiment of the invention entails the analysis of a Her-2 responsive gene set, in particular TGF-β regulated genes, to identify patients that will respond to Her-2 Ab, peptibody or small molecule drugs targeted against TGF-β sensitive or TGF-β resistant tumors. In this context, one skilled in the art may, for example, observe the pattern of a patient's Her-2 responsive gene set in a tissue sample in order to obtain information relating to the likely efficacy or biological effects of a specific therapeutic agent (or agents) targeting Her-2.

A specific embodiment of the invention consists of a method of examining a breast cell for evidence of a malignant phenotype comprising examining the mRNA expression profile of at least two mRNA polynucleotides in the cell. Identified herein are a variety of polynucleotides that are perturbed in breast cancer and are therefore useful targets for the profiling methods disclosed herein (see, e.g. Table I and FIG. 7). In a specific embodiment, the mRNA polynucleotides are selected from a first group of mRNA polynucleotides that are overexpressed in cells that overexpress Her-2/neu and a second group of mRNA polynucleotides that are underexpressed in cells that overexpress Her-2/neu, wherein the first group of mRNA polynucleotides hybridizes to a complementary polynucleotide of a gene selected from the group of genes identified by GenBank Accession numbers J03241, M60316, M81934, M29870, M15990, U83508, L03840, X02761, X51521, U29343 and X56807 and wherein the second group of mRNA polynucleotides hybridizes to a complementary polynucleotide of a gene selected from the group of genes identified by GenBank Accession numbers M65062, M92934, M19154, M62829, Z29083, X04434, K00650, M59040, L22548, X53587, AF000974 and Z18951; and wherein an mRNA expression profile in which the mRNA levels of the mRNA polynucleotides in the first group are increased greater than about 2 fold relative to the corresponding mRNA levels of the mRNA polynucleotides in normal breast cells and the mRNA levels of the mRNA polynucleotides in the second group are decreased greater than about 2 fold relative to the corresponding mRNA levels of the mRNA polynucleotides in normal breast cells is indicative of a malignant phenotype.

In preferred embodiments of the invention, the mRNA expression profile of at least one mRNA polynucleotide from the first group is examined and the mRNA expression profile of at least one mRNA polynucleotide from the second group is examined. In highly preferred embodiments, the mRNA expression profile of at least 3, 4, 5, 6, 7, 8, 9, 10 or all of the mRNA polynucleotides is examined. While the mRNA expression profile of genes can be evaluated by a wide variety of methods known in the art, in preferred embodiments, the mRNA expression profile is examined using a cDNA microarray or a filterarray such as those described in the Examples below.

Another related embodiments of the invention that pertains to the analysis of gene expression consists of a method for examining a breast cell for evidence of a malignant phenotype by comparing the level of mRNA expression of the gene identified by GenBank Accession No. M60316 with the level of mRNA of at least one comparative gene within the cell, wherein the comparative gene is selected from genes identified by GenBank Accession numbers D50683, M19154, M77349, M92934, AF031385, NM_000602 and J05593, and wherein an mRNA expression profile in which levels of M60316 mRNA are lower than those of the comparative gene is indicative of a malignant phenotype. In preferred embodiments of the invention, the level of M60316 mRNA expression is compared to 2, 3, 4, 5, 6, 7 or 8 comparative genes. In a further embodiment of the invention, the cytological characteristics of the cell are examined, preferably for mesenchymal characteristics and/ or epithelial characteristics. In this context, cells exhibiting a mRNA expression profile in which levels of M60316 mRNA are lower than those of the comparative gene exhibit mesenchymal characteristics. In contrast, cells exhibiting a mRNA expression profile in which levels of M60316 mRNA are higher than those of the comparative gene exhibit epithelial characteristics.

B. Methods for Using Profile Information to Characterize Mammalian Cancer Cell Biology The information obtained from the profiles described above is used to characterize specific aspects of cellular physiology that are associated with oncogenesis. For example, it is widely reported that TGF-β1 profoundly inhibits the growth of normal epithelial cells and that the proliferation of several breast cancer cell lines are significantly inhibited in vitro by TGF-β1. On the other hand, many cancer cells have escaped this TGF-β mediated growth inhibition by a variety of mechanisms. The microarray analysis and the transcript analysis in breast cancer cells provides evidence that HER-2/neu overexpression in these cells alters their responsiveness to exogenous TGF-β1.

Building upon the information obtained from the profile analysis, we tested directly whether overexpression of HER-2/neu affects the TGF-β signaling pathway by measuring the cell proliferation rates of CN vs. H2 overexpressing breast cancer cells in the presence of various concentrations of recombinant TGF-β1 using 2 independent methods of quantification: 1) direct cell counting and 2) crystal violet dye incorporation assays. As shown in the Examples below, a significant difference in TGF-β1 sensitivity was observed in the MCF-7/H2 cells compared to MCF-7/CN cells using the direct cell counting assay. In addition, MDA-MB-231/CN were found to be resistant to growth inhibition by TGF-β1, a finding which is consistent with previously published results. Not surprisingly, the MDA-MB-231/H2 cells were also resistant to inhibition by TGF-β1 and in fact, they appeared to be stimulated to pile up on each other and form obvious mounds. This effect was not observed in the MDA-MB-231/CN cells, even at relatively high concentrations of TGF-β (up to 20 ng/ml). Thus, this "piling" phenotype appears to require both TGF-β1 treatment and HER-2/neu overexpression.

Further expanding upon the models suggested by the profiling data, we determined that cells which contain the HER-2/neu amplicon are similarly resistant to TGF-β1 in vitro. Briefly, breast cancer cell lines containing the chromosome 17 HER-2/neu amplicon were analyzed for relative HER-2/neu protein levels and sensitivity to TGF-β. Moreover, the data obtained from the profiling and related experiments was used to develop a new method for inhibiting the growth of mammalian cancer cells, a method which has significant therapeutic implications.

As shown above, the invention provides cell-based assays which can be utilized for a variety of purposes. Representative embodiments of the invention include naturally occurring and physiologically relevant cell-line models of Her-2 overexpression stably transfected with LTR promoter constructs expressing human Her-2 or a control vector. The cell-lines include the MCF-7, BT-20, T47D MD-MB-231, HBL-100 and ZR75 breast tumor cell lines, the CaOV3 ovarian tumor cell-line and the LNCaP prostate cancer cell-line. In particular, one can utilize a Her-2 responsive gene set (e.g. TGF-β regulated genes) in such cell-based and animal assays to identify, develop and optimize methods and compositions (e.g. antibody, peptibody and small molecules) that target Her-2 overexpression or hyperactivity in human cancers. In this context, one skilled in the art may, for example, augment any cell-based and animal assays on the efficacy or biological effects of therapeutic agents targeting Her-2 with observations on the coordinate effect of such therapeutics on either an animal or a cell's responsiveness to TGF-β or its effect on TGF-β regulated genes. A representative embodiment of the invention entails the utilization of these cell based assays to evaluate direct or indirect TGF-β agonists to enhance antibody, peptibody or small molecule drugs targeting Her-2 overexpression or hyperactivity in human cancers.

Typical embodiments of these methods ate in vitro and/or in vivo cell based assays which compare the mRNA expression profile of a cell that is exposed to a molecule of interest with the mRNA expression profile of a control cell that has not been exposed to the molecule interest. In such comparisons, one typically evaluates changes in the mRNA expression profile that are correlated with a specific phenotype such as a malignant or transformed phenotype or a phenotype characterized by a more specific biological characteristic such as TGF-β sensitivity. In this way one can identify molecules which exhibit one or more desirable characteristics. For example, illustrative cell-based assays of the present invention are used to evaluate molecules (e.g. antibodies capable of inhibiting her-2/neu activation) which shift the mRNAs expression profile from a TGF-β resistant profile to a TGF-β sensitive profile.

C. Methods for Inhibiting the Growth of Mammalian Cells

Data obtained from the profiling experiments was expanded upon to develop methods for inhibiting the growth of mammalian cancer cells. Generally, the methods of the invention for inhibiting the growth of mammalian cells comprise exposing the cells to an effective amount of an antibody capable of inhibiting Her-2/neu receptor function and a TGF-β family member. Preferably, the amount of antibody capable of inhibiting Her-2/neu receptor function and a TGF-β family member employed will be amounts effective to synergistically inhibit cell growth. This can be accomplished in vivo or ex vivo in accordance, for instance, with the methods described below and in the Examples. Exemplary conditions or disorders to be treated with the antibody capable of inhibiting Her-2/neu receptor function and a TGF-β family member include benign or malignant cancer.

The invention disclosed herein has a number of embodiments pertaining to the inhibition of the growth of mammalian cells. A typical embodiment consists of a method of inhibiting the growth of mammalian cancer cells that overexpress Her-2/neu by exposing the mammalian cancer cells to a synergistically effective amount of an antibody capable of inhibiting Her-2/neu receptor function and a Transforming Growth Factor-β family member. The finding that an antibody capable of inhibiting Her-2/neu receptor function and a Transforming Growth Factor-β family member synergistically inhibit growth is unexpected because one could not predict the interrelationship between HER-2/neu overexpression and loss of growth inhibition by the TGF-β signaling pathway in cancer cells that is identified herein that contributes to the synergy observed in these methods. This surprising finding provides new therapeutic options that overcome limitations of methods employing the individual agents.

Another aspect of this method comprises inhibiting the growth of mammalian cancer cells that overexpress Her-2/ neu comprising exposing the mammalian cancer cells to a synergistically effective amount of an anti-Her-2/neu peptide mimetic and a Transforming Growth Factor-β family member selected from the group consisting of Transforming Growth Factor-β1 (TGF-β1), Transforming Growth Factor-β2 (TGF-β2) and Transforming Growth Factor-β3 (TGF-β3).

A related embodiment consists of a method of treating cancer in a mammal by administering to the mammal a synergistically effective amount of an antibody capable of inhibiting Her-2/neu receptor function and a Transforming Growth Factor-β family member selected from the group consisting of Transforming Growth Factor-β1 (TGF-β1), Transforming Growth Factor-β2 (TGF-β2) and Transforming Growth Factor-β3 (TGF-β3). While the growth of a variety of different mammalian cancer cell lineages that overexpress Her-2/neu can be inhibited by the disclosed methods, in the preferred embodiments of the invention, the mammalian cancer cells are breast cancer cells or ovarian cancer cells.

A number of antibodies capable of inhibiting Her-2/neu receptor function and Transforming Growth Factor-β family members can be employed in the methods for inhibiting cell growth that are disclosed herein. In preferred embodiments of the antibody utilized in these methods, the antibody binds to the Her-2 receptor epitope to which monoclonal antibody 4D5 (ATCC CRL 10463) binds and/or has the identifying biological characteristics of monoclonal antibody 4D5. In related embodiments, the antibody can have the binding affinity of monoclonal antibody 4D5 and/or comprises antigen binding region residues from monoclonal antibody 4D5. In preferred embodiments of the Transforming Growth Factor-β family member utilized in these methods, the Transforming Growth Factor-β family member is TGF-β1.

Doses of the antibody capable of inhibiting Her-2/neu receptor function and a TGF-β family member molecules preferably include pharmaceutical dosage units comprising an effective amount of antibody capable of inhibiting Her-2/neu receptor function and an effective amount of a TGF-β family member. By an effective amount is meant an amount sufficient to achieve a steady state concentration of these agents in vivo which results in a measurable reduction in any relevant parameter of disease and may include growth and/or invasion of primary or metastatic tumors, any accepted index of inflammatory reactivity, or a measurable prolongation of disease-free interval or of survival. For example, a reduction in tumor growth in 20% of patients is considered efficacious (Frei III, E., Cancer Journal 3:127–136 (1997)). However, an effect of this magnitude is not considered to be a minimal requirement for the dose to be effective in accordance with this invention. Effective doses and optimal dose ranges may be determined using the methods known in the art including those described herein.

D. Materials

The materials used to generate the gene expression analysis or "profile" of human breast cancer cells are commercially available. For the cDNA Microarrays, the Human Genome GEMS™ (GEM 1,2,3,4 and V) gene expression microarray available from Incyte were used. Each of Incyte's Human Genome Set of microarrays, contains more than 9,600 verified clones (over 40,000 when all GEMs considered) representing both known genes and ESTs. As a strategy to reduce redundancy, nearly all clones selected for the Human Genome GEM microarrays correspond to genes with identified 3' ends. The filter arrays were the 588 gene Cancer Atlas Blot filterarray membranes available from Clontech, (Cancer cDNA Expression Array (2), Catalog No. 7742-1). While these materials were used in the experiments disclosed herein, a variety of additional well known materials and methods for evaluating the profile of polynucleotides and polypeptides in mammalian cells are well known in the art and commercially available. For example, polynucleotide fragments of a gene are typically used as a primers and probes to evaluate and quantify the expression of genes in a cell such as cancer cells via PCR and Northern analysis respectively. See, e.g., Current Protocols In Molecular Biology, Volume 2, Unit 2, Frederick M. Ausubul et al. eds., 1995)).

The Transforming Growth Factor-β (TGF-β) family discussed in the context of the inventions disclosed herein consists of a group of structurally related proteins that are well known in the art. As used herein "TGF-β" or "TGF-β family" or "TGF-β family members" refer to the closely related polypeptides TGF-β1, TGF-β2 and TGF-β3. A variety of art references describe the cloning, expression and purification of TGF-β1 (see, e.g., Derynck et al. (1985) Nature 316: 701–705 and Gentry et al. (1987) Mol. Cell. Biol. 7: 3418–3427), TGF-β2 (see, e.g., deMartin et al. (1987) EMBO J. 6: 3673), and TGF-β3 (see, e.g., Derynck et al. (1988) EMBO J. 7: 3737–3743; Dijke et al. (1988) Proc. Natl. Acad. Sci. USA 85: 4715). In addition, TGF-β1, TGF-β2 and TGF-β3 are commercially available for use in a variety of purposes (see, e.g. R&D SYSTEMS as catalog numbers 240-B, 302-B2 and 243-B3 respectively).

The proteins in the TGF-β family regulate a wide range of crucial cell growth and differentiation events, including early embryonic patterning and morphogenesis, sexual organ and bone/cartilage formation, wound healing and immunosuppression and the disregulation of these events has been implicated in a variety of diseases including tumorigenesis. TGF-β family members signal through a heteromeric complexes of type I and type II serine/threomine kinase receptors, which consist of homologous single transmembrane serine/threonine kinases (for reviews, see Massague, J. et al., Trends in Cell Biology 4:172–178 (1994); Derynck, R., TIBS:548–553 (1994); Mathews, L. S., Endocr. Rev. 15:310–324 (1994); Heldin, C.-H., Cell 80:213–223 (1995)). Unlike most of the growth stimulatory factors, which mediate their cellular effects through homodimeric complexes of tyrosine kinase receptors (for reviews, see Schlessinger, J. and Ulrich, A., Neuron 9:383–391 (1992); Heldin, C.-H., Cell 80:213–223 (1995)), TGF-β family members require heteromeric complexes of both type I and type II serine/threonine kinase receptors for signaling (reviewed by Massague, J. et al., Trends in Cell Biology 4:172–178 (1994); Heldin, C.-H., Cell 80:213–223 (1995)).

Skilled artisans understand that equivalent molecules known in the art which mimic the inhibitory activity of a TGF-β family member are aspects of the presently disclosed methods which employ TGF-β family members. In particular, a number of molecules having transforming growth factor-beta activity are known in the art including amyloid beta-peptides (see, e.g. Huang et al., J Biol Chem 1998 Oct 16;273(42):27640–4), activated thyroglobulins (see, e.g. Huang et al., J Biol Chem 1998 Oct 2;273(40):26036–41) and pentacosapeptides homologous to retroviral envelope proteins (see, e.g. Huang et al., J Biol Chem 1998 Feb 27;273(9):4815–8). Consequently, such agonistic molecules can be examined in assays used to evaluate TGF-β1 activity and employed in appropriate equivalent methods as described herein.

The antibodies capable of inhibiting Her-2/neu receptor function which can be employed in the methods include the antibodies described in U.S. Pat. No. 6,165,464 to Hudziak et al., such as monoclonal antibodies 4D5, 3E8 and 3H4. Preferably the antibody is monoclonal antibody 4D5 (ATCC CRL 10463, deposited with the ATCC, 12301 Parklawn Drive, Rockville, Md. 20852 on May 24, 1990) or a biological equivalent thereof (e.g. HERCEPTIN). Alternatively, antibodies capable of inhibiting Her-2/neu receptor function can be generated by art accepted methods such as those discussed below.

Skilled artisans understand that equivalent molecules known in the art which mimic the inhibitory activity of an antibody capable of inhibiting Her-2/neu receptor function are aspects of the presently disclosed methods which employ an antibody capable of inhibiting Her-2/neu receptor function. Examples of such molecules include anti-HER2/neu peptide mimetics which disable P185HER2/neu tyrosine kinases which can inhibit the growth of at least a comparable or like manner to an antibody capable of inhibiting Her-2/ neu receptor function. For example, structure-based approaches have been used to develop a small (1.5 kDa) exocyclic anti-HER2/neu peptide mimic (AHNP) functionally similar to an anti-p185HER2/neu monoclonal antibody, 4D5 (HERCEPTIN). The AHNP mimetic specifically binds to p185HER2/neu with high affinity (KD=300 nM). This results in inhibition of proliferation of p185HER2/neu-overexpressing tumor cells, and inhibition of colony formation in vitro and growth of p185HER2/neu-expressing tumors in athymic mice. See, e.g., Park et al., Nat Biotechnol 2000 Feb;18(2):194–8.

1. Polyclonal Antibodies

The antibodies of the invention may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include a Her-2/neu polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation. The mammal can then be bled, and the serum assayed for antibody titer. If desired, the mammal can be boosted until the antibody titer increases or plateaus.

2. Monoclonal Antibodies

The antibodies of the invention may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include a Her-2/neu polypeptide or a fusion protein thereof, such as a Her-2/neu ECD-IgG fusion protein.

Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice,* Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. An example of such a murine myeloma cell line is P3X63AgU.1 described in Example 2 below. Human myeloma and mouse-human heteromyeloma cell lines also have been described for the production of human monoclonal antibodies [Kozbor, *J. Immunol.,* 133:3001 (1984); Brodeur et al., *Monoclonal Antibody Production Techniques and Applications,* Marcel Dekker, Inc., New York, (1987) pp. 51–63].

The culture medium in which the hybridoma cells are cultured can then be assayed for the presence of monoclonal antibodies directed against the Her-2/neu receptor. Preferably, the binding specificity of monoclonal antibodies produced by the hybridoma cells is determined by immunoprecipitation or by an in in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.,* 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium or RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody. Optionally, chimeric antibodies can be constructed which include at least one variable or hypervariable domain of an anti-Her-2/neu receptor antibody selected from the 4D5, 3E8 and 3H4 antibodies disclosed herein.

Optionally, the antibody capable of inhibiting Her-2/neu receptor function of the present invention will bind to the same epitope(s) as any of the 4D5, 3E8 and 3H4 antibodies disclosed herein. This can be determined by conducting various assays, such as described herein. For instance, to determine whether a monoclonal antibody has the same specificity as the 4D5, 3E8 and 3H4 antibodies specifically referred to herein, one can compare its activity in blocking assays or inhibition assays.

The antibodies of the invention include "cross-linked" antibodies. The term "cross-linked" as used herein refers to binding of at least two IgG molecules together to form one (or single) molecule. The Her-2/neu receptor antibodies may be cross-linked using various linker molecules and optionally the antibodies are cross-linked using an anti-IgG molecule, complement, chemical modification or molecular engineering. It is appreciated by those skilled in the art that complement has a relatively high affinity to antibody molecules once the antibodies bind to cell surface membrane. Accordingly, it is believed that complement may be used as a cross-linking molecule to link two or more antibodies bound to cell surface membrane. Among the various murine Ig isotypes, IgM, IgG2a and IgG2b are known to fix complement.

The antibodies of the invention may optionally comprise dimeric antibodies, as well as multivalent forms of antibodies. Those skilled in the art may construct such dimers or multivalent forms by techniques known in the art and using the anti-Her-2/neu receptor antibodies herein.

The antibodies of the invention may also comprise monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields an F(ab')$_2$ fragment that has two antigen combining sites and is still capable of cross-linking antigen.

The Fab fragments produced in the antibody digestion also contain the constant domains of the light chain and the first constant domain ($CH_1$) of the heavy chain. Fab' fragments differ from Fab fragments by the addition of a few residues at the carboxy terminus of the heavy chain $CH_1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

Single chain Fv fragments may also be produced, such as described in Iliades et al, *FEBS Letters,* 409:437–441 (1997). Coupling of such single chain fragments using various linkers is described in Kortt et al., *Protein Engineering,* 10:423–433 (1997).

In addition to the antibodies described above, it is contemplated that chimeric or hybrid antibodies may be prepared in etch using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

The Her-2/neu receptor antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature,* 321:522–525 (1986); Riechmann et al., *Nature* 332:323–329 (1988); and Presta, *Curr. Op. Struct. Biol.,* 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature,* 321:522–525 (1986); Riechmann et al., *Nature* 332:323–327 (1988); Verhoeyen et al., *Science* 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. Sources of such import residues or import variable domains (or CDRs) include the deposited anti-Her-2/neu receptor antibodies 4D5, 3E8 and 3H4 disclosed herein.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody [Sims et al., *J. Immunol.*, 151:2296–2308 (1993); Chothia and Lesk, *J. Mol. Biol.*, 196:901–917 (1987)]. Another method uses a particular framework derived from the consensus sequence of all human antibodies of a particular subgroup of light or heavy chains. The same framework may be used for several different humanized antibodies [Carter et al., *Proc. Natl. Acad. Sci. USA*, 89:4285–4289 (1992); Presta et al., *J. Immunol.*, 151:2623–2632 (1993)].

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding [see, WO 94/04679 published Mar. 3, 1994].

Human monoclonal antibodies may be made via an adaptation of the hybridoma method first described by Kohler and Milstein by using human B lymphocytes as the fusion partner. Human B lymphocytes producing an antibody of interest may, for example, be isolated from a human individual, after obtaining informed consent. For instance, the individual may be producing antibodies against an autoantigen as occurs with certain disorders such as systemic lupus erythematosus (Shoenfeld et al. *J. Clin. Invest.*, 70:205 (1982)), immune-mediated thrombocytopenic purpura (ITP) (Nugent et al. *Blood*, 70(1):16–22 (1987)), or cancer. Alternatively, or additionally, lymphocytes may be immunized in vitro. For instance, one may expose isolated human peripheral blood lymphocytes in vitro to a lysomotrophic agent (e.g. L-leucine-O-methyl ester, L-glutamic acid dimethly ester or L-leucyl-L-leucine-O-methyl ester) (U.S. Pat. No. 5,567,610, Borrebaeck et al.); and/or T-cell depleted human peripheral blood lymphocytes may be treated in vitro with adjuvants such as 8-mercaptoguanosine and cytokines (U.S. Pat. No. 5,229,275, Goroff et al.).

The B lymphocytes recovered from the subject or immunized in vitro, are then generally immortalized in order to generate a human monoclonal antibody. Techniques for immortalizing the B lymphocyte include, but ate not limited to: (a) fusion of the human B lymphocyte with human, murine myelomas or mouse-human heteromyeloma cells; (b) viral transformation (e.g. with an Epstein-Barr virus; see Nugent et al., supra, for example); (c) fusion with a lymphoblastoid cell line; or (d) fusion with lymphoma cells.

Lymphocytes may be fused with myeloma cells using a suitable fusing agent, such as polyethylene glycol, to form a hybridoma cell (Goding, *Monoclonal Antibodies: Principles and Practice*, pp. 59–103 (Academic Press, 1986)). The hybridoma cells thus prepared ate seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells. Suitable human myeloma and mouse-human heteromyeloma cell lines have been described (Kozbor, *J. Immunol.*, 133:3001 (1984); Brodeur et al., *Monoclonal Antibody Production Techniques and Applications*, pp. 51–63 (Marcel Dekker, Inc., New York, 1987)). Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp.59–103 (Academic Press, 1986)). Suitable culture media for this purpose include, for example, D-MEM or RPMI-1640 medium. The monoclonal antibodies secreted by the subclones are suitably separated from the culture medium, ascites fluid, or serum by conventional immunoglobulin purification procedures such as, for example, protein A chromatography, gel electrophoresis, dialysis, or affinity chromatography.

Human antibodies may also be generated using a non-human host, such as a mouse, which is capable of producing human antibodies. As noted above, transgenic mice are now available that are capable, upon immunization, of producing a full repertoire of human antibodies in the absence of endogenous immunoglobulin production. For example, it has been described that the homozygous deletion of the antibody heavy-chain joining region $J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255–258 (1993); Bruggermann et al., *Year in Immuno.*, 7:33 (1993); U.S. Pat. No. 5,591,669; U.S. Pat. No. 5,589,369; and U.S. Pat. No. 5,545,807. Human antibodies may also be prepared using SCID-hu mice (Duchosal et al *Nature* 355:258–262 (1992)).

In another embodiment, the human antibody may be selected from a human antibody phage display library. The preparation of libraries of antibodies or fragments thereof is well known in the art and any of the known methods may be used to construct a family of transformation vectors which may be introduced into host cells. Libraries of antibody light and heavy chains in phage (Huse et al., *Science*, 246:1275 (1989)) or of fusion proteins in phage or phagemid can be prepared according to known procedures. See, for example, Vaughan et al, *Nature Biotechnology* 14:309–314 (1996); Barbas et al., *Proc. Natl. Acad. Sci., USA*, 88:7978–7982 (1991); Marks et al., *J. Mol. Biol.*, 222:581–597 (1991); Hoogenboom and Winter, *J. Mol Biol.*, 227:381–388 (1992); Barbas et al., *Proc. Natl. Acad. Sci., USA*, 89:4457–4461 (1992); Griffiths et al., *EMBO Journal*, 13:3245–3260 (1994); de Kruif et al., *J. Mol. Biol.*, 248:97–105 (1995); WO 98/05344; WO 98/15833; WO 97/47314; WO 97/44491; WO 97/35196; WO 95/34648; U.S. Pat. No. 5,712,089; U.S. Pat. No. 5,702,892; U.S. Pat. No. 5,427,908; U.S. Pat. No. 5,403,484; U.S. Pat. No. 5,432,018; U.S. Pat. No. 5,270,170; WO 92/06176; WO 99/06587; U.S. Pat. No. 5,514,548; WO 97/08320; and U.S. Pat. No. 5,702,892. The antigen of interest is panned against the phage library using procedures known in the field for selecting phage-antibodies which bind to the target antigen.

The Her-2/neu receptor antibodies, as described herein, will optionally possess one or more desired biological activities or properties. Such antibodies may include but are not limited to chimeric, humanized, human, and affinity matured antibodies. As described above, the antibodies may be constructed or engineered using various techniques to achieve these desired activities or properties. In one embodiment, the Her-2/neu receptor antibody will have a Her-2/neu receptor binding affinity of at least $10^5$ $M^{-1}$, preferably at least in the range of $10^6$ $M^{-1}$ to $10^7$ $M^{-1}$, more preferably, at least in the range of $10^8$ $M^{-1}$ to $10^{12}$ $M^{-1}$ and even more preferably, at least in the range of $10^9$ $M^{-1}$ to $10^{12}$ $M^{-1}$. The binding affinity of the antibody can be determined without undue experimentation by testing the antibody in accordance with techniques known in the art, including Scatchard analysis (see Munson et al., supra). For example, a Her-2/neu receptor antibody can be assayed for binding affinity to the Her-2/neu-IgG receptor construct.

In another embodiment, the Her-2/neu receptor antibody of the invention may bind the same epitope to which 4D5, 3E8 and 3H4 binds, or bind an epitope on Her-2/neu which coincides or overlaps with the epitope to which 4D5, 3E8 and 3H4 binds, respectively. The antibody may also interact in such a way to create a steric conformation which prevents an antibody capable of inhibiting Her-2/neu receptor function binding to Her-2/neu. The epitope binding property of the antibody of the present invention may be determined using techniques known in the art.

3. Other Modifications

Other modifications of the Her-2/neu receptor antibodies and TGF-β family members are contemplated herein. The antibodies of the present invention may be modified by conjugating the antibody to a cytotoxic agent (like a toxin molecule) or a prodrug-activating enzyme which converts a prodrug (e.g. a peptidyl chemotherapeutic agent, see WO81/01145) to an active anti-cancer drug. See, for example, WO 88/07378 and U.S. Pat. No. 4,975,278. This technology is also referred to as "Antibody Dependent Enzyme Mediated Prodrug Therapy" (ADEPT).

The enzyme component of the immunoconjugate useful for ADEPT includes any enzyme capable of acting on a prodrug in such a way so as to covert it into its more active, cytotoxic form. Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; caspases such as caspase-3; D-alanylcarboxypeptidases, useful for converting prodrugs that contain D-amino acid substituents; carbohydrate-cleaving enzymes such as beta-galactosidase and neuraminidase useful for converting glycosylated prodrugs into free drugs; beta-lactamase useful for converting drugs derivatized with beta-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328: 457–458 (1987)). Antibody-abzyme conjugates can be prepared as described herein for delivery of the abzyme to a tumor cell population.

The enzymes can be covalently bound to the antibodies by techniques well known in the art such as the use of heterobifunctional crosslinking reagents. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., *Nature*, 312: 604–608 (1984).

Further modifications to the polypeptides of the invention are contemplated. For example, the antibodies or TGF-β family members may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, 16th edition, Oslo, A., Ed., (1980). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

4. Recombinant Methods

The invention also provides isolated nucleic acids encoding the antibody and TGF-β polypeptides disclosed herein, vectors and host cells comprising the nucleic acids, and recombinant techniques for the production of the polypeptides and antibodies which are well known in the art. See, e.g. Ausubel et al., Current Protocols in Molecular Biology, Wiley Interscience Publishers, (1995).

E. Formulations

The antibody capable of inhibiting Her-2/neu receptor function and the TGF-β family member are preferably administered in a carrier. The molecules can be administered in a single carrier, or alternatively, can be included in separate carriers. Suitable carriers and their formulations are described in *Remington's Pharmaceutical Sciences*, 16th ed., 1980, Mack Publishing Co., edited by Oslo et al. Typically, an appropriate amount of a pharmaceutically-acceptable salt is used in the carrier to render the formulation isotonic. Examples of the carrier include saline, Ringer's solution and dextrose solution. The pH of the solution is preferably from about 5 to about 8, and more preferably from about 7.4 to about 7.8. It will be apparent to those persons skilled in the art that certain carriers may be more preferable depending upon, for instance, the route of administration and concentration of agent being administered. The carrier may be in the form of a lyophilized formulation or aqueous solution.

Acceptable carriers, excipients, or stabilizers are preferably nontoxic to cells and/or recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; and/or non-ionic surfactants such as TWEEN™, PLURONICS™ or polyethylene glycol (PEG).

The formulation may also contain more than one active compound as necessary for the particular indication being treated, preferably those with complementary activities that do not adversely affect each other. Alternatively, or in addition, the composition may comprise a cytotoxic agent, cytokine or growth inhibitory agent. Such molecules are suitably present in combination in amounts that are effective for the purpose intended.

The antibody capable of inhibiting Her-2/neu receptor function and/or TGF-β family member may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drag delivery systems (for example, liposomes, albumin microspheres, microemulsions, nano-particles and nanocapsules) or in macroemulsions. Such techniques are disclosed in *Remington's Pharmaceutical Sciences* 16th edition, Oslo, A. Ed. (1980).

The formulations to be used for in vivo administration should be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and (ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods.

F. Modes of Adminstration

The antibody capable of inhibiting Her-2/neu receptor function and a TGF-β family member can be administered in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Optionally, administration may be performed through minipump infusion using various commercially available devices.

Effective dosages and schedules for administering an antibody capable of inhibiting Her-2/neu receptor function and a TGF-β family member may be determined empirically, and making such determinations is within the skill in the art. Effective dosage or amount of an antibody capable of inhibiting Her-2/neu receptor function used alone may range from about 1 μg/kg to about 100 mg/kg of body weight or more per day. An effective dosage or amount of a TGF-β family member used alone may range from about 1 mg/m$^2$ to about 150 mg/m$^2$. Interspecies scaling of dosages can be performed in a manner known in the art, e.g., as disclosed in Mordenti et al., *Pharmaceut. Res.*, 8:1351 (1991). Those skilled in the art will understand that the dosage of an antibody capable of inhibiting Her-2/neu receptor function and a TGF-β family member that must be administered will vary depending on, for example, the mammal which will receive the an antibody capable of inhibiting Her-2/neu receptor function and a TGF-β family member, the route of administration, and other drugs or therapies being administered to the mammal.

Depending on the type of cells and/or severity of the disease, about 1 μg/kg to 15 mg/kg (e.g. 0.1–20 mg/kg) of antibody is an initial candidate dosage for administration, whether, for example, by one or more separate administrations, or by continuous infusion. A typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. However, other dosage regimens may be useful.

It is contemplated that yet additional therapies may be employed in the methods. The one or more other therapies may include but are not limited to, other chemotherapies (or chemotherapeutic agents) and/or radiation therapy, immunoadjuvants, growth inhibitory agents, cytokines, and other non-Her-2 antibody-based therapies. Examples include interleukins (e.g., IL-1, IL-2, IL-3, IL-6), leukemia inhibitory factor, interferons, erythropoietin, thrombopoietin, and anti-VEGF antibody. Other agents known to inhibit the growth of mammalian cells -may also be employed, and such agents include TNF-α, CD30 ligand, 4-1BB ligand, and Apo-1 ligand.

Additional chemotherapies contemplated by the invention include chemical substances or drugs which are known in the art and are commercially available, such as Adriamycin, Doxorubicin, 5-Fluorouracil, Cytosine arabinoside ("Ara-C"), Cyclophosphamide, Leucovorin, Thiotepa, Busulfan, Cytoxin, Taxol, Toxotere, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Carrainomycin, Amimopterin, Dactinomycin, Mitomycins, Esperamicins (see U.S. Pat. No. 4,675,187), Melphalan and other related nitrogen mustards. Also included are agents that act to regulate or inhibit hormone action on tumors such as tamoxifen and onaptistone.

Preparation and dosing schedules for such chemotherapy may be used according to manufacturers' instructions or as determined empirically by the skilled practitioner. Preparation and dosing schedules for such chemotherapy are also described in Chemotherapy Service Ed., M. C. Perry, Williams & Wins, Baltimore, Md. (1992). The chemotherapeutic agent may precede, or follow administration with the antibody capable of inhibiting Her-2/neu receptor function and/or a TGF-β family member or may be given simultaneously therewith.

The chemotherapy is preferably administered in a carrier, such as those described above. The mode of administration of the chemotherapy may be the same as employed for the an antibody capable of inhibiting Her-2/neu receptor function or the TGF-β family member or it may be administered via a different mode.

Radiation therapy can be administered according to protocols commonly employed in the art and known to the skilled artisan. Such therapy may include cesium, iridium, iodine, or cobalt radiation. The radiation therapy may be whole body irradiation, or may be directed locally to a specific site or tissue in or on the body. Typically, radiation therapy is administered in pulses over a period of time from about 1 to about 2 weeks. The radiation therapy may, however, be administered over longer periods of time. Optionally, the radiation therapy may be administered as a single dose or as multiple, sequential doses.

An antibody capable of inhibiting Her-2/neu receptor function and a TGF-β family member (and one or more other therapies) may be administered concurrently or sequentially. Following administration of an antibody capable of inhibiting Her-2/neu receptor function and a TGF-β family member, treated cells in vitro can be analyzed. Where there has been in vivo treatment, a treated mammal can be monitored in various ways well known to the skilled practitioner. For instance, tumor mass may be observed physically, by biopsy or by standard x-ray imaging techniques.

III. Articles of Manufacture

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container can hold a polynucleotide for use in examining the mRNA expression profile of a cell as well as reagents used for this purpose.

The container can alternatively hold a composition which is effective for treating the condition and may have a sterile access port (for example the container may be an intravenous solution bag or a vial having a stopper pierceable by a hypodermic injection needle). The active agents in the composition are the an antibody capable of inhibiting Her-2/neu receptor function and a TGF-β family member. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may farther include other materials desirable from a commercial and user standpoint, including other buffers, diluents, filters, needles, syringes, and package inserts with instructions for use.

The following examples are offered by way of illustration and not by way of limitation. The disclosures of all citations in the specification are expressly incorporated herein by reference.

EXAMPLES

Example 1

Methods and Materials of the Invention

Cell lines

The HER-2/neu engineered cell lines (MCF-7/H2, BT-20/H2, ZR-75-1/H2), as is known in the art were generated by repeated infections with a retroviral vector containing the human, full-length HER2/neu cDNA. Matching control cell lines were generated for each by simultaneous infection with the empty viral vector. The SKBR-3, BT-474, MDA-MB-361, MDA-MB-175 and MDA-MB-453 cell lines were obtained from the American Type Tissue Collection. Cells were cultured in RPMI 1640 or DMEM (MDA-MB-361 and MDA-MB-175) supplemented with 10% fetal bovine serum (FBS), 100 U ml$^{-1}$ penicillin (P) and 100 U ml$^{-1}$ streptomycin at 37° C. in a humidified, 5% $CO_2$ atmosphere.

RNA Preparation

For microarray analysis and the initial verification Northern blots (FIG. 2), total cellular RNA was purified by guanidinium/cesium chloride ultracentrifugation from freshly trypsinized cells. The polyA RNA was selected using oligo dT magnetic beads (Dynal). For the Northern blot experiments with TGF-β1 treatments (FIG. 5), total RNA was purified directly from monolayer cultures using the Trizol reagent (Gibco).

Microarray Analysis cDNA microarrays: Total RNA was isolated from semi-confluent MCF-7/CN and MCF-7/H2 cells grown under standard culture conditions. Poly(A) selected RNA was then isolated and used as the template to generate flourochrome (Cy3 and Cy5) labeled cDNA which were hybridized simultaneously to the Synteni/Incyte GEMS 1–4, and V (about 40,000 elements). Balanced differential expression differences greater than 2.5 fold were considered. For the filter arrays. $^{32}$P labeled cDNA probes were separately synthesized to the identical MCF-7/CN and H2 poly (A) RNA pair that was utilized in the Synteni/Incyte. Two identical 588 gene filterarray membranes (Cancer Atlas Blot; Clontech, Cancer cDNA Expression Array (2), Catalog No. 7742-1) were hybridized and the signals were quantified by phosphorimager analysis. The probe synthesis/labeling and probing of the filters was carried out on two separate occasions to assay for variability in filters and technique. Genes reproducibly scoring in both experiments with differences greater than 2.0 fold were considered differentially expressed.

Northern Blotting cDNA probes were generated by PCR amplification from mixed tissue cDNA libraries for the indicated genes using gene specific primers. Total RNA (8 to 10 ug) was electrophoresed in 1% glyoxyl gels and transferred to positively charged nylon membranes (Ambion) using the Turbo Blotter apparatus (Schleicher and Schuell) and the Northern Max-Gly (Ambion) buffers. The purified cDNA inserts were random primed using $\alpha^{32}$P-dATP.

Cell Proliferation Assays

Direct cell counting assays: Cells were trypsinized, counted and seeded at 8000 cells/well in multiple 12 well plates. Cells were allowed to settle and attach for 12–18 hr after which treatments were begun (=day 0). On the indicated days, triplicate well were harvested by trypsinization and counted using a Coulter counter.

Crystal Violet assays: 96 well plate format. A wide range (from 0.03 to 20 ng/ml) of TGF-β1 concentrations were also tested in the crystal violet assay. A relatively steep dose response was observed with concentrations below 0.1 ng/ml having very little effect on proliferation and concentration above about 1.0 ng/ml showing nearly maximum inhibition.

Antibodies, Cytokines and Protein Lysate Preparation

Anti p15INK4B and cdk4 (C-22) antibodies were from Santa Cruz, $p21^{CIP1}$ (clone 70) from Transduction labs, p27KIP1 (clone G173–524) from Pharmingen. Western blots of HER-2 using c-neu Ab-3 (Oncogene Research Products).

HERCEPTIN was purchased from Genentech. HERCEPTIN (Trastuzumab) is a recombinant DNA-derived humanized monoclonal antibody that selectively binds with high affinity in a cell-based assay (Kd=5 nM) to the extracellular domain of the human epidermal growth factor receptor 2 protein, HER2. The antibody is an $IgG_1$ kappa that contains human framework regions with the complementarity-determining regions of a murine antibody (4D5) that binds to HER2. The humanized antibody against HER2 is produced by a mammalian cell (Chinese Hamster Ovary) [CHO] suspension culture in a nutrient medium containing the antibiotic gentamicin. Gentamicin is not detectable in the final product. HERCEPTIN is a sterile, white to pale yellow, preservative-free lyophilized powder for intravenous (IV) administration. The nominal content of each HERCEPTIN vial is 440 mg Trastuzumab, 9.9 mg L-histidine HCl, 6.4 mg L-histidine, 400 mg trehalose dihydrate, and 1.8 mg polysorbate 20, USP. Reconstitution with only 20 mL of the supplied Bacteriostatic Water for Injection (BWFI), USP, containing 1.1% benzyl alcohol as a preservative, yields a multi-dose solution containing 21 mg/mL Trastuzumab, at a pH of approximately 6.

See http://www.gene.com/products/herceptin/insert.html.

TGF-β1 treatments-recombinant, human (Cho cell derived) TGF-β1 (R&D systems) was diluted in acidified PBS containing 1% BSA.

Lysates: Semi-confluent cells were harvested with trypsin, counted, pelleted, washed with PBS and resuspended in modified RIPA buffer (PBS containing 1.0% Triton X-100, 0.1% SDS, and a cocktail of protease inhibitors (1 mM PMSF (phenylmethylsulfonyl fluoride), 10 μg/ml leupeptin and 20 μg/ml aprotinin) at a concentration of $2$–$4 \times 10^6$ cells/ml. Lysates were vortexed, incubated on ice for 15 min and passed through 28 g needles and cleared of insoluble cellular debris by centrifugation.

Western Blotting

Protein samples were boiled in SDS sample buffer containing β-mercaptoethanol, subjected to SDS-PAGE on 6,8 or 10% acrylamide gels and transferred to PVDF membranes. All buffers, gels and membranes were purchased from Novex. After transfer, the membranes were blocked for several hr with TBS-T containing 9% nonfat dry milk (TBS-T is saline buffered with 25 mM Tris-HCl (H 7.4) containing 0.1% Tween-20). Primary antibodies were diluted in TBS-T+1% milk and incubated with blots overnight at 4 C. After several washes, the blots were incubated with a 1:2000 dilution of goat-anti-mouse-HRP (Santa Cruz) or 1:4000 dilution of goat-anti-rabbit transduction Labs). Antibody complexes were detected with the ECL chemiluminescent system (Amersham) or the Dura chemiluminescent reagents (Pierce).

Example 2

Profiling Mammalian Breast Cancer Cells

In order to profile mammalian breast cancer cells, the expression profile of MCF-7/H2 cells was compared to that of MCF-7/CN cells using both microarrays (GEM1, 2, 3, 4,V; Synteni/Incyte) and filterarrays (Atlas Cancer Array; Clontech)(FIG. 1). Using the Synteni/Incyte cDNA microarrays, approximately 490 elements were scored as showing differences of greater than 2.5 fold in hybridization signals in MCF-7/H2 compared to MCF-7/CN cDNA. Roughly half (274) of the differentially expressed sequences represent full-length and, in most cases, previously published genes. Due to the redundancy of elements on the arrays, these changes represent differential expression of 189 individual genes with 115 genes showing higher expression in MCF-7/CN and 74 showing higher expression in MCF-7/H2. The filterarray experiments yielded 59 differentially expressed genes 21 of which were also found to be differentially expressed using the microarrays. Here, we focus the analysis on groups of genes that are likely to act in distinct molecular pathways.

Components of Ative TGF-β Signaling are Downregulated by HER-2/Neu Overexpression In the profiles generated herein, several TGF-β superfamily ligands and receptors showed significantly altered expression in the MCF-7/H2 cells (FIG. 1). We detected differential expression of 5 TGF-β ligands (TGF-β2, TGF-β3, BMP-3, BMP-5 and BMP-7) and 2 receptors, the TGF-β type II receptor (TBRII) (in et al., Cell 68, 775–85 (1992); Lin et al., Mol Reprod Dev 32, 105–10 (1992) and Massague, J. Cell 69, 1067–70 (1992) and the type III receptor (endoglin) (Yamashita, H., et al. J Biol Chem 269, 1995–2001 (1994); Letamendia, A., et al. J Biol Chem 273, 33011–9 (1998) and Barbara et al.,. J Biol Chem 274, 584–94 (1999)). This prompted us to query the array data for genes reported to be activated in response to TGF-β. We identified eight such genes in the data set that had significantly lower transcript levels in the MCF-7/H2 cells (TGFβ targets in FIG. 1). A unifying theme of the normal function of these genes is the regulation of extracellular matrix (ECM) deposition and remodeling. The products of the eight TGF-β inducible target genes (see FIG. 1) include alpha-1 collagens (Type III, V, XVIII); CTGF and Cyr61 cysteine rich secreted proteins Bork, P. FEBS Lett 327, 125–30 (1993); Grotendorst, G. R. Cytokine Growth Factor Rev 8, 171–9 (1997). Brunner et al.,. DNA Cell Biol 10, 293–300 (1991) and Kireeva et al., Mol Cell Biol 16, 1326–34 (1996). TGFβ1/β-Ig-H3/kerato-epithelin a secreted protein that has a role in cell-collagen adhesion interactions (Skonier, J., et al. DNA Cell Biol 11, 511–22 (1992), Timp-2, an inhibitor of metalloproteinases (such as collagenases) (Stetler-Stevenson et al.,. J Biol Chem 265, 13933–8 (1990) and Petrella et al., Miner Electrolyte Metab 24, 136–43 (1998)) and Endothelin 1 (ET-1) a secreted protein with potent vasoconstrictive properties. Several of these genes have themselves been implicated in cancer biology. Timp-2 is considered to be an anti-metastasis gene due to its ability to inhibit proteases and the ET-1 protein induced by TGF-β1 in epithelial cancer cells has been implicated in tumor progression. The consistent suppression of TGF-β activated genes in response to HER-2/neu overexpression provides evidence that TGF-β signaling is inhibited in MCF-7/H2 cells.

Components Antagonizing TGF-β Signaling are Upregulated by HER-2/Neu Overexpression Evi-1 (ectopic viral integration site protein 1, Nucifora, G. *Leukemia* 11, 2022–31 (1997)), is a transcriptional repressor that has oncogenic potential when mutated or overexpressed (see, e.g., Bartholomew et al., *Oncogene* 14, 569–77 (1997) and Hirai, H. *Int J. Biochem Cell Biol* 31, 1367–71 (1999)) is upregulated 3.4 fold by HER-2/neu overexpression. One relevant function of Evi-1 is its ability to block TGF-β1 induced gene transcription by inhibiting SMAD3 (see, e.g., Kutokawa, M., et al *Nature* 394, 92–6 (1998) and Roberts, A. B. *Microbes Infect* 1, 1265–73 (1999)). We also identified a novel gene (hTRT-1) that potentially antagonizes TGF-β function and is strongly upregulated, up to 13 fold, by HER-2/neu. The sequence identified for the hTRT element (clone 23915) overlaps with a 6.1 kb KIAA1051 sequence (GenBank AB029874) which appears to be a novel gene (see, e.g., Nagase, T., et al *DNA Res* 6, 337–45 (1999)). A blast search with KIAA1051 yielded only one other match (89% identity over 866 nucleotides) with mink TRT1 (GenBank U00594) (Ralph et al., *Proc Natl Acad Sci USA* 90, 10710–4 (1993)). TRT1 is a transcript down-regulated by TGF-β1 in mink lung epithelial (Mv1Lu) cells. Thus, we refer to this sequence as a potential TGF-β1 repressible target gene (FIG. 1, hTRT1).

We next determined whether the influence of HER-2/neu on the TGF-β response markers identified in the array analysis was peculiar to MCF-7 cells or if it was a reproducible, cell line-independent effect. Total RNA was isolated from five additional pairs of HER-2/neu overexpressing (H2) and vector controls (CN) breast cell-lines (BT-20, ZR-75-1, T47D, MDA-MB-231 and HBL-100) grown under standard culture conditions. The expression levels of HER-2 (FIG. 2a) and eight TGF-β response markers (FIG. 2b) were examined in MCF-7/CN and MCF-7/H2 as well as the five additional CN and H2 cell lines. Expression of seven TGF-β markers genes from the array data (FIG. 1) along with the well-characterized TGF-β inducible gene, PAI-1 were analyzed by Northern blotting and/or Taqman RT-PCR. First, without taking into consideration the effects of HER-2, the overall expression pattern of these 8 genes in the CN cell lines appears to delineate two distinct types with respect to the TGF-β pathway. The first, (Type A), was characterized by low level expression of the TGF-β receptor (TBRII) and the TGF-β2 ligand, moderate to low expression of the downstream target genes BIGH3, CTGF, Cyr61, PAI-1 and TIMP-2, and relatively high expression of BMP-7 (FIG. 2b; light gray bars in upper panels). The control cell lines that displayed the Type A profile are MCF-7/CN, BT-20/CN, ZR-75-1/CN, and T47D/CN. The cells displaying the second profile (Type B), which is essentially the opposite of the type A profile, includes the MDA-MB-231/CN and HBL-100/CN. These cells were found to overexpress TBRII and the TGF-β2 ligand, as well as downstream target genes (BIGH3, TIMP-2, CTGF, Cyr61 and PAI-1) while BMP-7 was essentially undetectable (FIG. 2b; dark gray bars in upper panels). The significance of the BMP-7 expression pattern is not known, but it is striking that when the other TGF-β markers appear low (Type A) BMP-7 is quite highly expressed, whereas in the type B cells which have high levels of TBRII, TGF-β2 and other target genes , BMP-7 was barely detectable. The distinction between the two transcriptional profiles appears to correlate with phenotypic differences. The Type A cells tend to retain epithelial characteristics, generally growing in clumps of cobblestone shaped cells whereas the Type B cells are more mesenchymal (i.e. elongated, motile individual cells). Importantly, TGF-β was shown to be a critical mediator of the epithelial to mesenchymal transition EMT) described in progression of several epithelial cancer models.

The response of most (⅞) of the TGF-β markers to HER-2/neu overexpression was similar in the MCF-7, BT-20 and ZR-75-1 cells (Type A members) despite their diverse genetic and biological properties (FIG. 2b, bars in lower panels). Reduced message levels were observed for TBRII, TGF-β2, BIGH3, TIMP-2, CTGF, Cyr61, and PAI-1, whereas, the expression of BMP-7 varied independently in these three cell lines. In contrast, the TGF-β marker levels were generally unaffected (gray bars, upper bar graphs) or elevated (bars having whole number values, lower bar graphs) in response to HER-2/neu in the MDA-MB-231 and HBL-100 cells Type B group). Although T47D/CN cells displayed a Type A expression profile, the marker alterations in response to HER-2/neu overexpression were more similar to the Type B pattern. We have also qualitatively confirmed the MCF-7 CN vs. H2 microarray data for BMP-5, endoglin (lower in MCF-7/H2 cells) and hTRT1 (higher in MCF-7/H2 cells) by Northern blotting or PCR. Taken together, these results provide evidence that TGF-β transcriptional programs are altered in a relatively consistent manner in response to HER-2/neu overexpression in breast tumor cell-lines, however the response can vary depending on the cell line model. This is especially obvious for cells that express low levels of TGF-β ligands/receptors (Type A) versus cells that appear to be vigorously stimulated by autocrine signaling due to TGF-β ligand/receptor overexpression (Type B).

While not being bound by a specific theory, the microarray expression data suggests several possible mechanisms by which HER-2/neu may interfere with signaling in the TGF-β pathway. Since lower levels of the type II receptor (TBRII) and the co-receptor endoglin were detected, it is possible that the HER-2/neu overexpressing cells are unable to efficiently bind ligand. Another possibility is that the increased expression of Evi-1, which has been shown to inhibit SMAD3 DNA binding is responsible for the lack of TGF-β responses. Additionally, if the hTRT-1 is truly a TGF-β repressed transcript, then high levels of normally repressed hTRT-1 could possibly have inhibitory effects on TGF-β signaling. Finally, since it is well established that ras is activated by type I receptor tyrosine kinases, including HER-2/neu, it may be that SMAD3 nuclear localization is inhibited in a similar manner to what has been observed with oncogenic ras. (see, e.g., Kretzschmar M, Genes Dev 1999 Apr 1;13(7):804–16).

Figure 6A:
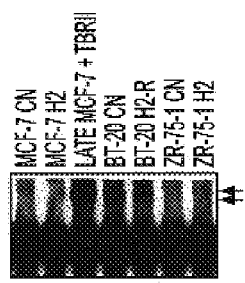
FIGS. 6A–6C. Effects of HER-2/neu on TBRII levels, ligand binding and SMAD phosphorylation/nuclear import. a Type A breast cancer cells have low TBRII protein levels. The TBRII protein was immunoprecipitated using the rabbit (L-21, Santa Cruz) antibody from whole cell lysates of the indicated cell lines. After SDS-PAGE, TBRII was detected by western blotting using the rabbit (C-16, Santa Cruz) antibody. The black arrow indicates the position of the TBRII protein doublet which was verified using a cell extract from late passage MCF-7 cells transfected with the full length TBRII cDNA. The light gray arrow points to a slightly larger protein which may be non-specific. The heavy band marked by an asterisks is heavy chain IgG. b Ligand binding is similar in MCF-7/CN and MCF-7/H2 cells. The binding of FITC-labeled TGF-β1 was examined by FACS analysis of live single cell suspensions using the TGF-β1 Fluorokine kit (R&D Systems) according to manufacture's instructions. The green curves shows the intensity of cells in the FL1 channel after incubation with FITC-TGF-β1. The red curves represents the fluorescence of untreated cells and the purple curves represents the fluorescence of cells incubated with an FITC labeled protein control. The fold shift in the median intensity of the FL1 signal in the TGF-β1 treated cells compared to the controls is indicated in the upper tight hand corner of each panel, (CN: 2.12 fold; H2: 2.32 fold). c Overexpression of HER-2 does not prevent phosphorylation of SMAD2 in response to TGF-β1. Western blots of whole cell extracts using a phospho-specific anti-SMAD2 antibody (Upstate Biotechnologies).
Figures 1, 6B:
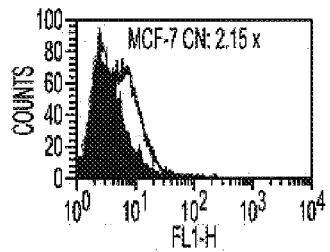
Figures 2, 6B:
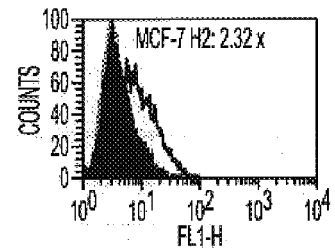

Building upon the foundation provided by the profile, we examined several aspects of the TGF-β pathway by measuring ligand binding, TBRII protein levels, as well as phosphorylation and nuclear translocation of the SMAD proteins in order to evaluate these mechanistic possibilities. A two-fold decrease in TBRII message levels was detected in MCF-7/H2 cells compared to CN cells by cDNA microarray and this result was verified by Northern blotting (1.9 fold decrease; FIG. 2). However, the transcript level in the MCF-7 CN cells as well as in the ZR-75-1 cells was low relative to BT-20 and especially to MB-231 and HBL-100 cells. To determine if these differences were reflected in the protein level we performed immunoblot analysis with numerous commercially available antibodies against TBRII. We were unable to detect an unambiguous signal with any of the antibodies by direct Western blotting. However, when a combination of antibodies were used to immunoprecipitate TBRII prior to immunoblotting, a signal was detectable inn the BT-20 CN and H2 cells as well as in a positive control lysates (FIG. 6a) consisting of a subclone of MCF-7 cells transfected with the TBRII cDNA (ref). From these assays, it was concluded that the level of TBRII protein in BT-20 cells was just at the limit of detection and that the difference between BT-20 CN and H2 was not obvious. The TBRII protein levels in MCF-7 and ZR-75-1 cells are extremely low, preventing confirmation of lower protein levels in the H2 lines. These levels do, however appear to be sufficient for TGF-β1 mediated growth arrest in MCF-7 cells as well as TGF-β1 mediated induction of many genes in both cell lines.

Figure 6C:
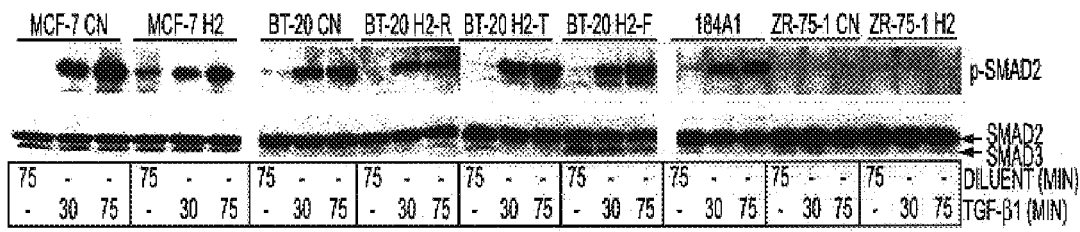

Ligand binding was measured in MCF-7/CN and MCF-7/H2 cells using FITC-labeled TGF-β1 and FACS analysis. Clear evidence of TGF-β1 binding was obtained in both cell lines as indicted by a 2.1 to 2.3 fold shift in median fluorescence (FL1-H) upon addition of FITC-labeled TGF-β1 to live, single cell suspensions (green curves, FIG. 6b). This binding was specific, as the shift in fluorescence was completely blocked by excess unlabeled TGF-β1 or by pre-incubation of the FITC-TGF-β1 with anti-TGF-β1 antibodies. In addition, no shift in fluorescence was observed with a labeled irrelevant protein compared to untreated cells (purple curves and red curves respectively; FIG. 6b). Although no significant difference in ligand binding was detected in MCF-7/CN compared to MCF-7/H2 cells, this assay is not an accurate measure of TGF-β1 complexed with active signaling receptors since co-receptors, such endoglin and betaglycan may also account for the TGF-β1 bound to the cell surface. Thus, another measure of activated receptors was sought. Ligand binding to TBRII results in recruitment and activation of the type I receptor. The type I receptor, in turn, phosphorylates receptor activated signal transduction mediators, R-SMADs, which in the case of TGF-β1 signaling, are SMAD2 and SMAD3. An antibody specific for the phosphorylated form of SMAD2 was used to assay lysates from cells treated with TGF-β1 for relatively short time periods (30 to 75 min). As shown in FIG. 6c, phospho-SMAD2 was clearly detected after 30 min of treatment with TGF-β in the MCF-7 CN cells. Although, consistently somewhat reduced compared to the CN cells, phospho-SMAD2 could be reproducible detected in the MCF-7 H2 as well. In addition, the BT-20 cells (CN as well as H2 clones R, T and F) all showed significant levels of phospho-SMAD2 upon TGF-β1 treatment. Overall, the differences in phosphorylation of were modest and did not appear sufficient to account for the large differences in TGF-β1 responses observed in these cells. Surprisingly, no phospho-SMAD2 was detected in the ZR-75-1 (CN or H2) cells upon TGF-β1 treatment despite the fact that SMAD2 protein was readily detected in ZR-75-1 cells. The positive control for this experiment was the 184A1 cell line which are non-malignant, chemically transformed breast epithelial cells (ref) which show extreme sensitivity to growth inhibition by TGF-β and high levels of phosphorylated SMAD2 (FIG. 6c).

Given the observation that phospho-SMAD2 was detectable in most of the TGF-β1 stimulated cells, we next analyzed whether or not SMAD2 was translocated to the nucleus after cells were exposed to TGF-β1 and whether the level of phosphorylation correlated with the efficiency of nuclear localization. Using immunocytochemistry, both with enzymatic DAB staining and fluorescence, we show that endogenous SMAD2 translocates to the nucleus equally well in MCF-7/CN and MCF-7/H2 cells upon treatment with TGF-β1 for 1 hr (FIG. 6d). We also found that SMAD2 was concentrated in the nucleus after TGF-β1 treatment in BT-20/CN, BT-20/H2, MB-231/CN and MB-231/H2 cells. The ZR-75-1/CN and H2 cells on the other hand, showed no appreciable differences in SMAD2 localization upon treatment with TGF-β1. Therefore, at least in the cells examined in this study, phosphorylation of SMAD2 correlated well with its accumulation in the nucleus after TGF-β1 stimulation. In summary, the analysis of SMAD protein activation suggests that HER-2/neu overexpression does not prevent ligand binding, receptor activation or SMAD2/(3?) phosphorylation and nuclear accumulation. Thus, the defect in HER-2/neu overexpressing cells may occur downstream of SMAD nuclear accumulation, perhaps at the level of SMAD DNA binding or interactions with other DNA-binding partners.

Example 3

Using Profile Information to Characterize Mammalian Cancer Cell Biology

Insensitivity of HER-2/neu Overexpressing Breast Cancer Cells to TGF-β1

Figure 3A:
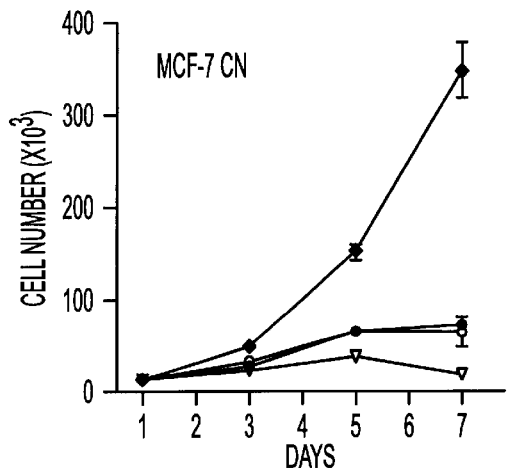
FIGS. 3A–3G. HER-2/neu overexpression alters biological responses of breast cancer cells to TGF-β. a–d MCF-7/CN and MCF-7/H2 cells were treated with diluent control or the indicated concentrations of TGF-β1. Cells were trypsinized and counted with a Coulter counter on days 1, 3 and 7 after treatment. Each point represents the average of triplicate wells (+/− standard deviation for error bars). a The growth of MCF-7/CN cells is severely inhibited by TGF-β1. The symbols for each treatment group are as follows: diluent (♦), 0.2 ng/ml TGF-β1 (○), 0.4 ng/ml TGF-β1 (●), 0.8 ng/ml TGF-β1 (▽). b MCF-7/H2 cells are resistant to growth inhibition by TGF-β1. The symbols are the same as in a. c Comparison of MCF-7 CN (○) vs. H2 (♦) cells treated with 0.2 ng/ml TGF-β1. Proliferation data from a and b are displayed as % of diluent treated controls. d Comparison of MCF-7 CN (○) vs. H2 (♦) cells treated with 0.8 ng/ml TGF-β1. e p185-HER-2 levels in control and engineered HER-2 overexpressing cells. Western blot analysis of 40 ug of total cell extract for the indicated cell lines using an anti-HER-2 monoclonal antibody (top panels) and an anti-β-tubulin antibody (bottom panel) as a control for protein loading. A HER-2 protein doublet is visible in both engineered and naturally HER-2 overexpressing cell lysates (see FIG. 5). f Effects of HER-2 on TGF-β response in a panel of breast cancer cells. Crystal violet dye incorporation assays were performed on quadruplicate wells of cells treated with 2 ng/ml of TGF-β1 or diluent control for 6 days. Each bar represents the value of the TGF-β1 treated wells as a percentage of diluent controls. Error bars signify the standard deviation calculated from at least 2 separate experiments. The MCF-7/Par and CN lines showed similar levels of inhibition indicating that particularly sensitive clones had not been selected during the retroviral transfection and subsequent cell culture of the CN lines. g TGF-β1 induces a "piling" phenotype in HER-2/neu overexpressing MB-231 cells. MDA-MB-231/CN and H2 cells were seeded on chambered slides and grown for 5 days in the presence of 5 ng/ml of TGF-β1 or diluent control. Cells were then fixed and stained with crystal violet dye in methanol and photographed with a 20×(top 4 panels) or a 60×(bottom 2 panels) objective.
Figure 3B:
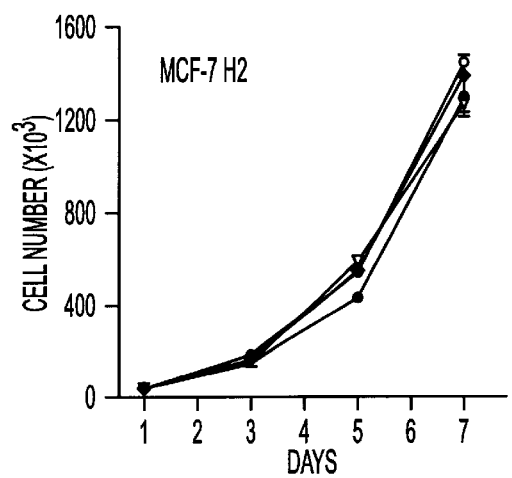
Figure 3C:
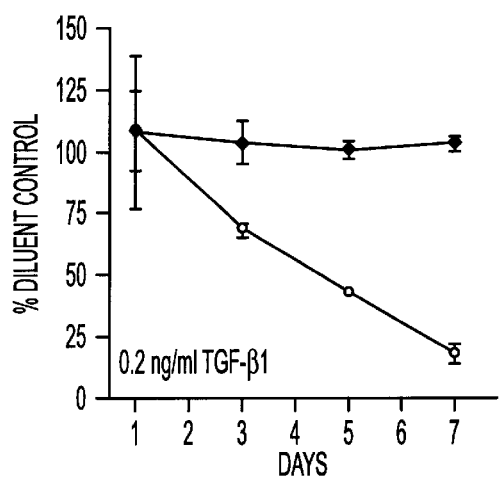
Figure 3D:
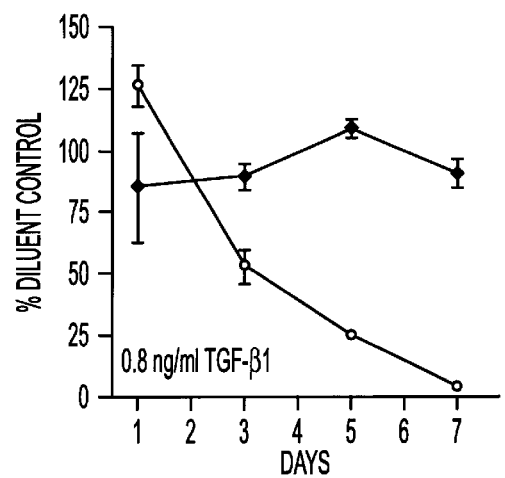
Figure 3E:
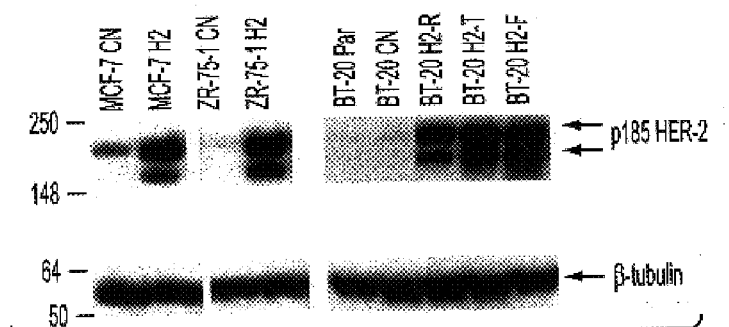

It is widely reported that TGF-β1 profoundly inhibits the growth of normal epithelial cells and that the proliferation of several breast cancer cell lines are significantly inhibited in vitro by TGF-β1. On the other hand, many cancer cells have escaped this TGF-β mediated growth inhibition by a variety of mechanisms described in the art. Our microarray analysis and the transcript analysis in the other breast cell lines raises the possibility that HER-2/neu overexpression in MCF-7, BT-20 and ZR75-1 cells would alter their responsiveness to exogenous TGF-β1. We therefore tested directly whether overexpression of HER-2/neu affects the TGF-β signaling pathway by measuring the cell proliferation rates of CN vs. H2 overexpressing breast cancer cells in the presence of various concentrations of recombinant TGF-β1 using 2 independent methods of quantification: 1) direct cell counting and 2) crystal violet dye incorporation assays. A significant difference in TGF-β1 sensitivity was observed in the MCF-7/H2 cells compared to MCF-7/CN cells using the direct cell counting assay (FIGS. 3a–d). The diluent treated control cells grew logarithmically (a 49 fold increase in cell number) over the 7 days of treatment whereas cells exposed to TGF-β1 (from 0.2 to 0.8 ng/ml) showed at most a 7 fold increase in cell number (FIG. 3a). In contrast, the effect of TGF-β1 on MCF-7/H2 cells was minimal, with the diluent and the TGF-β1 treated MCF-7/H2 cells all increasing in number by about 60 fold over 7 days (FIG. 3b). In the presence of 0.2 ng/ml (FIG. 3c) or 0.8 ng/ml TGF-β1 (FIG. 3d), MCF-7/CN cells were inhibited by 80% and 95% respectively whereas the MCF-7/H2 cells showed at most 8% inhibition. Thus, it appears that HER-2/neu overexpression can render breast cancer cells resistant to growth inhibition by TGF-β1.

Figure 3F:
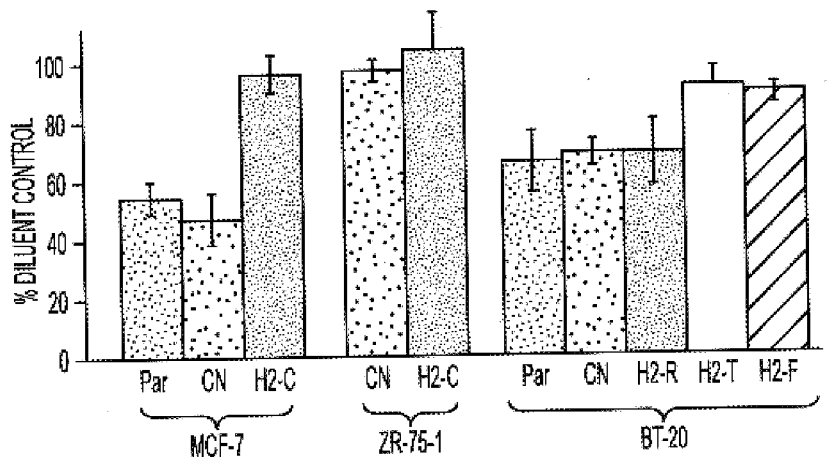

The crystal violet dye incorporation assay was also used to expand the analysis of TGF-β1 response to additional breast tumor cell lines engineered to overexpress HER-2. Consistent with the cell counting assays, a significant difference in TGF-β1 sensitivity was observed between the non-transfected MCF-7 parental line (Par) and MCF-7/CN (46–53% inhibition) and their H2 overexpressing counterparts (<10% inhibition)(FIG. 3f). However, the differences in cell growth are not as pronounced as in the cell counting assay. HER-2/neu overexpression induced similar alterations in the expression profiles of TGF-β1 responsive genes in ZR-75-1/H2 and MCF-7-H2 (FIG. 2b). Nonetheless, unlike MCF-7 cells, ZR-75-1/CN cells appear resistant to TGF-β1 mediated growth inhibition in the absence of HER- 2/neu overexpression. ZR-75-1/Par, CN as well as H2 cells were all resistant to growth inhibition by TGF-β1 in both the crystal violet and cell counting assays (FIG. 3f). These data are consistent with a published report implicating overexpression of mdm2 as the critical mediator of TGF-β resistance in certain breast cancer cells, including ZR-75-1 cells. BT-20/Par and CN cells were sensitive to TGF-β1 in this assay (inhibited by 32–34%) but to a lesser degree than MCF-7 cells. Three different BT-20/H2 clones with increasing levels of HER-2/neu protein expression were also examined, (clones R, T and F). The BT-20/H2 clones with the highest HER-2/neu levels (clone T and F) did show a small but significant decrease in TGF-β sensitivity (10–12% inhibition) compared to Par and CN cells. The third BT-20/H2 clone (clone R) which expresses at least 2 fold less HER-2/neu protein than T and F, did not show a significant decrease in sensitivity. In summary, we observe large difference in the sensitivity of MCF7 cells, no difference in the sensitivity of ZR75 cells, and small difference in the sensitivity of BT20 cells. These results correlate very well with and may explain the different degrees of proliferation rate changes in the three different cells lines.

Figure 3G:
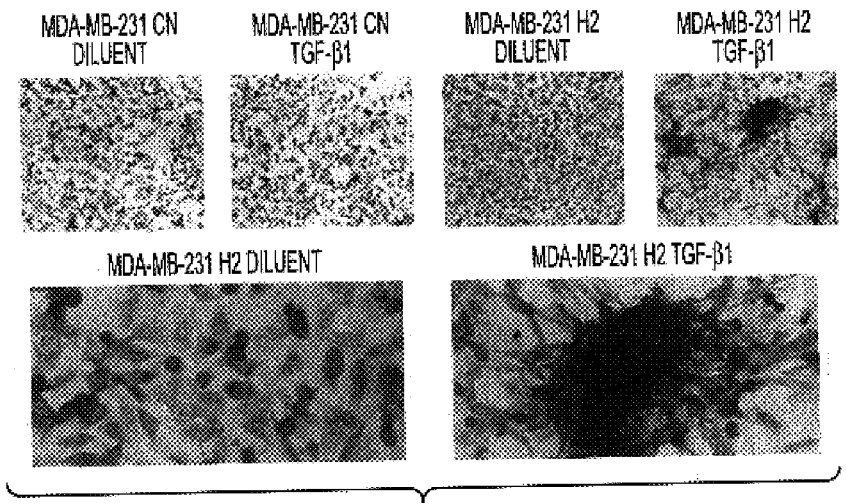

MDA-MB-231/CN were resistant to growth inhibition by TGF-β1 in the crystal violet assay which is consistent with previously published results. Not surprisingly, the MDA-MB-231/H2 cells were also resistant to inhibition by TGF-β1 and in fact, they appeared to be stimulated to pile up on each other and form obvious mounds (FIG. 3g). This effect was not observed in the MDA-MB-231/CN cells, even at relatively high concentrations of TGF-β (up to 20 ng/ml). Thus, this "piling" phenotype appears to require both TGF-β1 treatment and HER-2/neu overexpression.

HER-2/neu Overexpression Inhibits Gene Activation by Exogenous TGF-β1

Figure 4A:
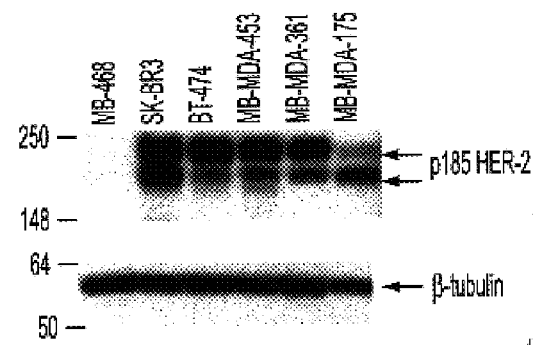
FIGS. 4A–4D. HERCEPTIN sensitizes naturally overexpressing HER-2 cells to growth inhibition by TGF-β. a HER-2 protein levels in naturally HER-2 overexpressing cell lines. Western blot analysis of p185-HER-2 in total cell lysates (40 ug of protein) for the indicated cell lines using an anti-HER-2 monoclonal antibody (top panels) and an anti-β-tubulin antibody (bottom panel) as a control for protein loading. b The growth of most naturally overexpressing HER-2 breast cancer cell lines is not inhibited by TGF-β1 treatment in vitro. The indicated cells were assayed by crystal violet dye incorporation in quadruplicate wells after treatment with 2 ng/ml of TGF-β1 or diluent control for 6 days. Each bar represents the value of the TGF-β1 treated wells as a percentage of diluent controls. Error bars signify the standard deviation calculated from at least 2 separate experiments. c–d HERCEPTIN renders SKBR3 and MDA-MB-361 cells more sensitive to the growth inhibition by TGF-β1. SKBR3 (c) or MDA-MB-361 (d) were pretreated for 48 hrs with 5 ug/ml of human normal IgG1 or HERCEPTIN and seeded at 8000 cells/well in 12 well plates. After attaching overnight, the pretreatment groups were divided in half and treated with either diluent control or 2 ng/ml TGF-β1 and counted on the indicated days. The media was changed every other day and replaced with fresh IgG or HERCEPTIN along with either diluent or TGF-β1. Triplicate wells of each treatment group were trypsinized and counted on a Coulter counter on the indicated days. The data is shown as the % of each pretreatment group control, (thus (○) equals TGF-β1+ NIgG cell number/Diluent+ NIgG cell number)*100) and (●) equals TGF-β1+ HERCEPTIN cell number/Diluent+ HERCEPTIN cell number)*100). Each bar represents the mean of triplicate wells+/− standard deviation.
Figure 4B:
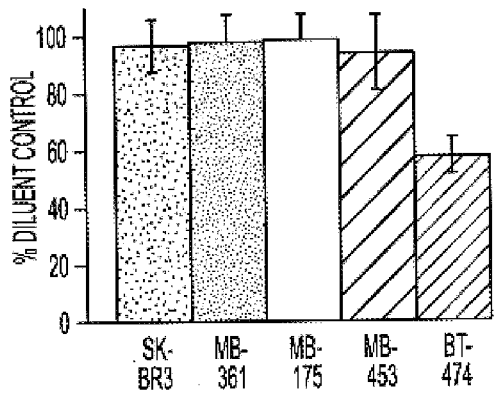
Figure 4C:
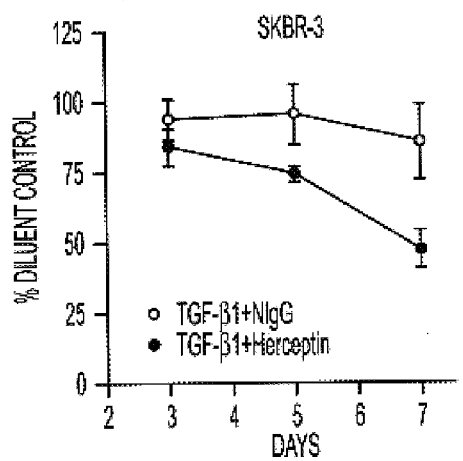

Heretofore, in proposing a connection between HER-2/neu overexpression and inhibition of TGF-β dependent gene responses, we had assumed that endogenous TGF-β synthesis and exogenous TGF-β present in fetal bovine serum is responsible for maintaining the TGF-β transcriptional program in CN breast tumor cells in culture. In an attempt to directly demonstrate that HER-2/neu overexpression inhibits TGF-β1 inducible gene activation, the mRNA expression levels of CTGF, PAI-1 and BIGH3 in breast cancer cells treated with 2 ng/ml recombinant TGF-β1 for 8 hr and 24 hr was compared to cells treated with the diluent alone. The MCF-7/CN, BT-20/CN and ZR-75-1/CN control lines each showed increased levels of CTGF which peaked after 8 hr of treatment with TGF-β1 and thereafter declined by 24 hr (FIG. 4a). It is evident in the RNA gel blot autoradiogram that little or no induction of CTGF in response to TGF-β1 was observed in any cell line that overexpressed HER-2/neu. Activation of PAI-1 and BIGH3 in the CN lines was also apparent after 8 hr of TGF-β1 exposure, however, the levels of the markers continued to increase after 24 hr of treatment. Quantitative estimates of the relative mRNA levels of CTGF, PAI-1 and BIGH3 in CN and H2 cells derived from phosphoimager analysis of RNA gel blots is represented by the histograms in FIG. 4b. The induction by TGF-β1 of all three TGF-β markers is either substantially repressed or undetectable in each of the H2 cell lines (gray bats). Expression of a fourth marker, the cdk4 inhibitor, p15$^{INK4B}$, which has been shown to be a central mediator of cell cycle arrest induced by TGF-β1 in a number of cell line models such as MvLu1 mink lung epithelial cells was also examined. As shown in FIG. 4c, the p15$^{INK4B}$ protein is dramatically induced while the level of cdk4 itself was not appreciably changed in MCF-7/CN cells upon up to 52 hr of TGF-β1 treatment. In contrast, induction was not observed in two separate experiments in which MCF-7/H2 cells were treated in the same manner. These data provide evidence that the cell cycle arrest seen in the MCF-7/CN cells could be mediated by p15$^{INK4B}$ and its induction is abrogated in the HER-2/neu overexpressing cells. Despite the fact that ZR-75 CN cells are resistant to growth inhibition by TGF-β1, p15$^{NK4B}$ is detectable in the control cells and is stimulated further by TGF-β1 treatment. In contrast, the level p15$^{NK4B}$ protein is barely detectable in ZR-75-1/H2 cells with or without TGF-β1 stimulation. It is possible that ZR-75-1 parental and vector control cells may be resistant to TGF-β, despite the induction of p15$^{NK4B}$, by virtue of elevated mdm2 levels acting downstream of cdk inhibitors (ref). The p15$^{NK4B}$, gene is reported to be mutated in BT-20 cells (ref) and consistent with this, we did not observe a protein product at the appropriate size in BT-20 cell lysates with the p15$^{NK4B}$ antibody. This suggests that induction of p15$^{NK4B}$ is not absolutely required for TGF-β mediated growth arrest since proliferation of BT-20 cells is affected by TGF-β albeit to a lesser degree than MCF-7 CN or parental cells. In summary, the above data show that overexpression of HER-2/neu consistently prevents or greatly reduces the activation of at least four markers in response to exogenous TGF-β1.

Figure 4D:
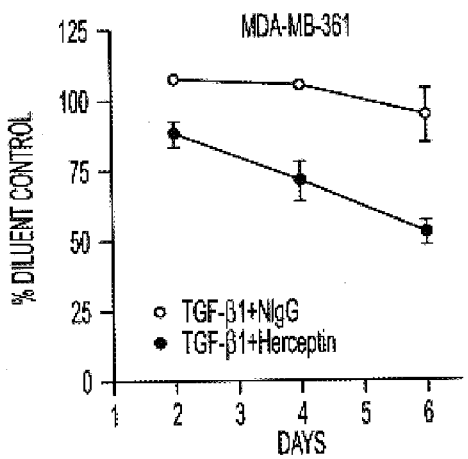

In order to determine if the effects of HER-2/1neu on TGF-β1 inducible gene expression was restricted to a few genes or whether it was a global consequence, a cDNA microarray experiment was undertaken to profile the expression changes induced by TGF-β1 in MCF-7/CN and MCF-7/H2 cells. A total of 174 elements were found to be induced ≧1.9 fold by exposure of MCF-7/CN cells to 2 ng/ml of TGF-β1 for 24 hrs (FIG. 4d) whereas no TGF-β1 repressed genes were detected under these conditions. Remarkably, no genes were either induced or repressed by TGF-β1 treatment in the MCF-7/H2 cells (FIG. 4d). Although we may have failed to detect alterations of early response genes activated or repressed within the first several hours of TGF-β1 treatment, these results, taken together with the individual analysis of CTGF, PAI-1, BIGH3 and p15$^{NK4B}$ formally demonstrate that HER-2/neu overexpression inhibits TGF-β1 inducible gene activation. Moreover, the comprehensive nature of this effect provides strong evidence that the transcriptional blockade occurs at critical regulatory juncture in the TGF-β signaling pathway.

TGF-β1 Resistance in Breast and Ovarian Cancer Cells Containing the HER-2/Neu Amplicon As engineered overexpression of the HER-2/neu gene can block sensitivity to TGF-β1 growth control, we tested to determine whether cells which contain the HER-2/neu amplicon are similarly resistant to TGF-β1 in vitro. Five breast cancer cell lines (SKBR-3, MB-MDA-361, MB-MDA-175, MB-MDA-453 and BT-474) that have been described as containing the chromosome 17 HER-2/new amplicon were analyzed for relative HER-2/neu protein levels and sensitivity to TGF-β. SKBR3 cells are reported to have about 2 million molecules of p185HER-2 on their cell surface and as shown in FIG. 5a contain the highest levels of HER-2 protein of any cell line tested. The other naturally overexpressing cell lines contain approximately ⅓ to ⅛ as much HER-2 protein as the SKBR3 cells however these amounts (i.e. in MB-MDA-175) are still significantly above the levels expressed by cells with normal copy numbers of the HER-2/new gene (i.e. MB-468 cells). These 5 cell lines were examined in crystal violet proliferation assays in the presence of 2 ng/ml TGF-β1 or diluent control for 6 days. The percent of diluent treated control was calculated for each cell line (FIG. 5b). No significant decrease in cell proliferation was observed in 5 out of the 6 cell lines tested. The same was true for TGF-β1 concentrations of up to 10 ng/ml. In contrast, BT-474 cells were sensitive to growth inhibition by TGF-β1 (~43% inhibition).

Example 4

Synergistic Inhibition of Tumor Growth by an Antibody Capable of Inhibiting HER-2/Neu Receptor Function and a TGF-β Family Member HERCEPTIN Significantly Increases Responsiveness of HER-2 Overexpressing Cells to TGF-β1

Figure 5C:
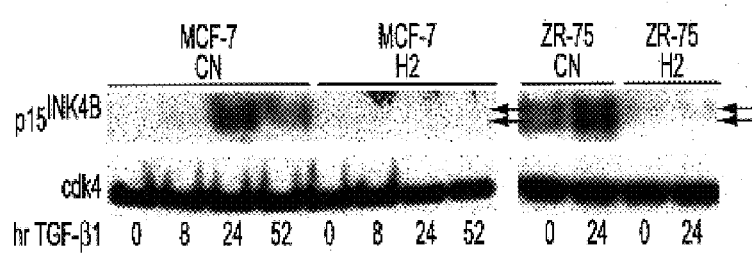
Figure 5D:
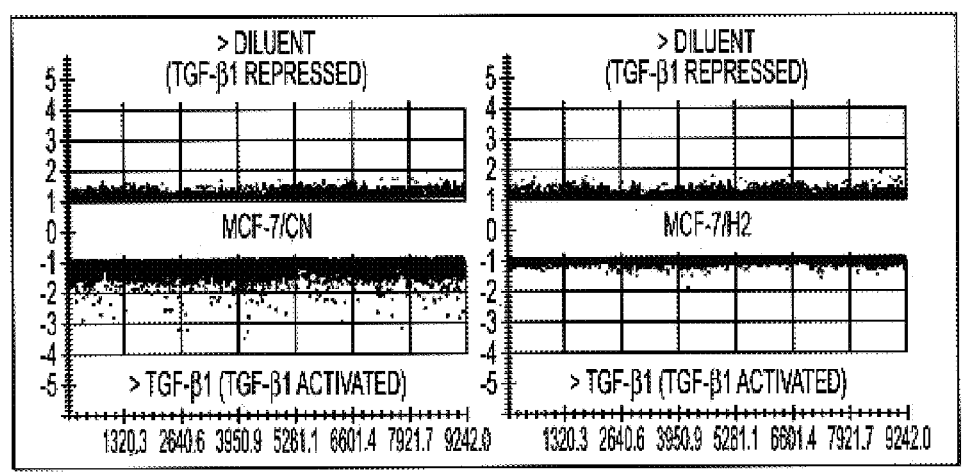

In order to evaluate the effects of a combination of the anti-HER-2/neu antibody antagonist HERCEPTIN and TGF-β, short-term proliferation assays with and without HERCEPTIN were performed. SKBR-3 and MDA-MB-361 cell lines were chosen for this experiment since they are readily growth inhibited by short-term HERCEPTIN treatment in vitro. The cells were pre-treated with either normal human IgG1 or HERCEPTIN for 48–72 hr and then counted and plated at equal densities in presence of normal IgG or HERCEPTIN. Half of each pretreatment group was treated with TGF-β1 and the other half with the diluent alone. Even after 6–7 days of treatment, the SKBR3 and MDA-MB-361 cells treated with normal IgG1 and TGF-β1 showed very little inhibition (<10%) compared to IgG1 treatment alone (FIGS. 5b–c). SKBR3 and MDA-MB-361 cells treated with HERCEPTIN and TGF-β1, on the other hand, were significantly inhibited (47–52%) compared to HERCEPTIN treated control cells. HERCEPTIN treatment also increased the sensitivity of MDA-MB-453 to TGF-β1 by 35%. Therefore, even over a relatively short time period, treatment with an anti-HER-2 antibody partially reverses the apparent TGF-β1 resistance displayed in the natural HER-2/neu overexpressing cells in vitro.

The engineered HER-2/neu overexpressing cells (i.e. MCF-7/H2) are growth inhibited to different degrees by short-term HERCEPTIN treatment in vitro as the "natural" HER-2/neu overexpressing cells. This difference is not yet understood, however, growth of these engineered cells in long term experiments as xenografts in nude mice is greatly inhibited by HERCEPTIN. In any case, no significant increase in TGF-β sensitivity was observed in MCF-7/H2 cells upon treatment with HERCEPTIN.

Throughout this application, various publications are referenced. The disclosures of these publications are hereby incorporated by reference herein in their entireties. The foregoing written description is considered to be sufficient to enable one skilled in the art to practice the invention. The present invention is not to be limited in scope by the example presented herein. Indeed, various modifications of the invention in addition to those shown and described herein will become apparent to those skilled in the art from the foregoing description and fall within the scope of the appended claims.

TABLE I

Representative Genes Identified in Gene Expression Analysis Methods

| Art Accepted Designation(s) (fold difference in expression relative to control) | GenBank Accession No. See, e.g.: http://www.ncbi.nlm.nih.gov or http://bioinformatics. weizmann.ac.il/cards/ | Representative Art Reference/Source |
|---|---|---|
| TGF-BETA3 3.40 | J03241 | Dijke et al., Proc. Natl. Acad. Sci. U.S.A. 85 (13), 4715–4719 (1988). |
| BONE MORPHOGENETIC PROTEIN 7 (OSTEOGENIC Prot1) 4.45 | M60316 | Celeste et al., Proc. Natl. Acad. Sci. U.S.A. 87, 9843–9847 (1990) |
| IGFBP5 −2.2 | M65062 | Kiefer et al., Biochem. Biophys. Res. Commun. 176 (1), 219–225 (1991) |
| CONNECTIVE TISSUE GROWTH FACTOR −5.16 | M92934 | Bradham et al., J. Cell Biol. 114 (6), 1285–1294 (1991) |
| TRANSFORMING GROWTH FACTOR-BETA-2 −2.10 | M19154 | Madisen et al., DNA 7 (1), 1–8 (1988) |
| EARLY GROWTH RESPONSE PROTEIN 1(EGR-1) KROX24 −2.01 | M62829 | Shimizu et al., J. Biochem. 111, 272–277 (1992) |
| 5T4 ONCOFETAL ANTIGEN −2.32 | Z29083 | Myers et al., J. Biol. Chem. 269 (12), 9319–9324 (1994) |
| INSULIN-LIKE GROWTH FACTOR I RECEPTOR −2.42 | X04434 | Ullrich et al., EMBO J. 5 (10), 2503–2512 (1986) |
| cdc25B; M-PHASE INDUCER PHOSPHATASE 2 3.90 | M81934 | Galaktionov et al., Cell 67 (6), 1181–1194 (1991) |
| RAS-RELATED C3 BOTULINUM TOXIN SUBST (P21-RAC1 2.19 | M29870 | Didsbury et al., J. Biol. Chem. 264, 16378–16382 (1989) |
| YES 3.97 | M15990 | Sukegawa et al., Mol. Cell. Biol. 7, 41–47 (1987) |
| C-fos −5.61 | K00650 | van Straaten et al., Proc. Natl. Acad. Sci. U.S.A. 80 (11), 3183–3187 (1983) |

TABLE I-continued

Representative Genes Identified in Gene Expression Analysis Methods

| Art Accepted Designation(s) (fold difference in expression relative to control) | GenBank Accession No. See, e.g.: http://www.ncbi.nlm.nih.gov or http://bioinformatics. weizmann.ac.il/cards/ | Representative Art Reference/Source |
|---|---|---|
| ANGIOPOIETIN-1 4.20 | U83508 | Davis et al., Cell 87 (7), 1161–1169 (1996) |
| FGFR4 2.30 | L03840 | Ron et al., J Biol Chem. 15;268(8):5388–94 (1993) |
| Fibronectin 14.48 | X02761 | Kornblihtt et al., Proc. Natl. Acad. Sci. U.S.A. 80 (11), 3218–3222 (1983) |
| Ezrin (cytovillin 2) 2.70 | X51521 | Gould et al., EMBO J. 8 (13), 4133–4142 (1989) |
| HYALURONAN RECEPTOR (RHAMM) 3.95 | U29343 | Wang et al., Gene 174 (2), 299–306 (1996) |
| DSC2 mRNA for desmocollins type 2a and 2b 7.63 | X56807 | Parker et al., J. Biol. Chem. 266 (16), 10438–10445 (1991) |
| Cell adhesion molecule (CD44) −2.10 | M59040 | Harn et al., Biochem. Biophys. Res. Commun. 178 (3), 1127–1134 (1991 |
| Collagen type XVIII alpha −3.30 | L22548 | Oh et al., Genomics 19 (3), 494–499 (1994) |
| Integrin beta4 D4g −2.43 | X53587 | Tamura et al., J. Cell Biol. 111 (4), 1593–1604 (1990) |
| Zyxin related protein ZRP-1D5 −10.02 | AF000974 | Murthy et al., J. Biol. Chem. 274 (29), 20679–20687 (1999) |
| Caveolin-1 −4.00 | Z18951 | Glenney et al., FEBS Lett. 314 (1), 45–48 (1992) |
| Vascular endothelial growth factor - related clone{IMAGE:488697} See FIG. 7 | AA045970.1 | This clone is available royalty-free through LLNL; contact the IMAGE Consortium (info@image.llnl.gov) for further information. |
| Gamma-glutamyltransferase 1 - related clone {IMAGE:359931} See FIG. 7 | AA062961.1 | This clone is available royalty-free through LLNL; contact the IMAGE Consortium (info@image.llnl.gov) for further information. |
| SH3-binding domain glutamic acid-rich protein like {IMAGE:488908} See FIG. 7 | AA057023.1 | This clone is available royalty-free through LLNL; contact the IMAGE Consortium (info@image.llnl.gov) for further information. |
| Prospero-related homeobox 1 {IMAGE:220293} See FIG. 7 | H82136.1 | This clone is available royalty-free through LLNL; contact the IMAGE Consortium (info@image.llnl.gov) for further information. |
| Cytochrome P450, subfamily IIJ (arachidonic acid eposygenase) polypeptide 2 {IMAGE:245490} See FIG. 7 | N72507.1 | This clone is available royalty-free through LLNL; contact the IMAGE Consortium (info@image.llnl.gov) for further information. |
| KIAA0936 protein {IMAGE:144805} See FIG. 7 | 144805 | Graves et al., Proc. Natl. Acad. Sci. U.S.A. 82 (6), 1653–1657 (1985) |
| ESTs{IMAGE:321925} See FIG. 7 | W37595.1 | This clone is available royalty-free through LLNL; contact the IMAGE Consortium (info@image.llnl.gov) for further information. |
| ESTs {IMAGE:470547} See FIG. 7 | 470547 | Pasquali et al., J. Clin. Invest. (1994) In press |

TABLE I-continued

Representative Genes Identified in Gene Expression Analysis Methods

| Art Accepted Designation(s) (fold difference in expression relative to control) | GenBank Accession No. See, e.g.: http://www.ncbi.nlm.nih.gov or http://bioinformatics. weizmann.ac.il/cards/ | Representative Art Reference/Source |
|---|---|---|
| ESTs {IMAGE:624490} See FIG. 7 | AA186508.1 | This clone is available royalty-free through LLNL ; contact the IMAGE Consortium (info@image.llnl.gov) for further information. |
| ESTs {IMAGE:469999} See FIG. 7 | AA029106.1 | This clone is available royalty-free through LLNL ; contact the IMAGE Consortium (info@image.llnl.gov) for further information. |
| ESTs {IMAGE:307220} See FIG. 7 | W21538.1 | This clone is available royalty-free through LLNL ; contact the IMAGE Consortium (info@image.llnl.gov) for further information. |
| *Homo sapiens* bone morphogenetic protein 5 (BMP-5) See FIG. 1 | M60314 | Celeste et al., Proc. Natl. Acad. Sci. U.S.A. 87, 9843–9847 (1990) |
| Human bone morphogenetic protein-3 See FIG. 7 | M22491 | Wozney et al., Science 242 (4885), 1528–1534 (1988) |
| TGF-betaIIR alpha See FIG. 1 | D50683 | Ogasa et al., Gene 181 (1–2), 185–190 (1996) |
| Endoglin See FIG. 7 | X72012 | Bellon et al., Eur. J. Immunol. 23 (9), 2340–2345 (1993) |
| Transforming growth factor-beta induced gene product (BIGH3) See FIG. 1 | M77349 | Skonier et al., DNA Cell Biol. 11 (7), 511–522 (1992) |
| Metalloproteinase-2 inhibitor (TIMP-2) See FIG. 1 | J05593 | Stetler-Stevenson et al., J. Biol. Chem. 265 (23), 13933–13938 (1990) |
| Endothelin-1 See FIG. 1 | J05008 | Inoue et al., J. Biol. Chem. 264 (25), 14954–14959 (1989) |
| Pro-alpha-1 type 3 collagen See FIG. 1 | X14420 | Ala-Kokko et al., Biochem. J. 260 (2), 509–516 (1989) |
| Pro-alpha-1 (V) collagen See FIG. 1 | M76729 | Greenspan et al., J. Biol. Chem. 266 (36), 24727–24733 (1991) |
| Evi-1 See FIG. 1 | S82592 | Ogawa et al., Oncogene 13 (1), 183–191 (1996) |
| HTRT-1 See FIG. 1 | AB028974 Mink TRT1 (U00594) | Nagase, T., et al. DNA Res 6, 337–45 (1999) |
| Type XVIII collagen See FIG. 1 | AF018081 | Saarela et al., Matrix Bio. 16 (6), 319–328 (1998) |
| PAI-1, Serine (or cysteine) proteinase inhibitor, clade E (nexin, plasminogen activator inhibitor type 1), member 1 (SERPINE1) See FIG. 1 | NM_000602 | Ny T et al., Proc. Natl. Acad. Sci. U.S.A. 83 (18), 6776–6780 (1986) |
| Cyr61 protein See FIG. 1 | AF031385 | Chen et al., J. Biol. Chem. 275, 24953–24961. |

What is claimed is:

1. A method of inhibiting the growth of mammalian breast cancer cells that overexpress Her-2/neu comprising exposing the mammalian breast cancer cells to a therapeutically effective amount of an antibody that binds to a Her-2/neu epitope to which monoclonal antibody 4D5 (ATCC CRL 10463) binds and a Transforming Growth Factor-β family member selected from the group consisting of Transforming Growth Factor-β1 (TGF-β1), Transforming Growth Factor-β2 (TGF-β2) and Transforming Growth Factor-β3 (TGF-β3).

2. The method of claim 1 wherein the antibody comprises antigen binding region residues from monoclonal antibody 4D5 (ATCC CRL 10463) and human antibody residues.

3. The method of claim 1, wherein the Transforming Growth Factor-β family member is TGF-β1.

4. The method of claim 1, wherein said mammalian cancer cells are exposed to the antibody prior to the Transforming Growth Factor-β family member.

5. The method of claim 1 wherein said antibody has the binding affinity of monoclonal antibody 4D5 (ATCC CRL 10463).

6. The method of claim 1 wherein the antibody has an antigen-binding region of monoclonal antibody 4D5 (ATCC CRL 10463).

7. A method of treating breast cancer in a mammal having a breast cancer that overexpresses Her-2/neu comprising administering to the mammal a therapeutically effective amount of an antibody that binds to a Her-2/neu epitope to which monoclonal antibody 4D5 (ATCC CRL 10463) binds and a Transforming Growth Factor-β family member selected from the group consisting of Transforming Growth Factor-β1 (TGF-β1), Transforming Growth Factor-β2 (TGF-β2) and Transforming Growth Factor-β3 (TGF-β3).

8. A method of inhibiting the growth of mammalian breast cancer cells that overexpress Her-2/neu comprising exposing the mammalian breast cancer cells to a therapeutically effective amount of Transforming Growth Factor-β1 (TGF-β1) and of an antibody that inhibits Her-2/neu receptor function, wherein the antibody that inhibits Her-2/neu receptor function binds a Her-2neu receptor epitope to which monoclonal antibody 4D5 (ATCC CRL 10463) binds.

9. The method of claim 8 wherein the antibody comprises an amino acid sequence from a complementarity determining region of monoclonal antibody 4D5 (ATCC CRL 10463) and an amino acid sequence from a framework region of a human antibody.

10. A method of inhibiting the growth of mammalian breast cancer cells that overexpress Her-2/neu comprising exposing the mammalian breast cancer cells to a therapeutically effective amount of Transforming Growth Factor-β2 (TGF-β2) and of an antibody that inhibits Her-2/neu receptor function, wherein the antibody that inhibits Her-2/neu receptor function binds a Her-2/neu receptor epitope to which monoclonal antibody 4D5 (ATCC CRL 10463) binds.

11. The method of claim 10 wherein the antibody comprises an amino acid sequence from a complementarity determining region of monoclonal antibody 4D5 (ATCC CRL 10463) and an amino acid sequence from a framework region of a human antibody.

12. A method of inhibiting the growth of mammalian breast cancer cells that overexpress Her-2/neu comprising exposing the mammalian breast cancer cells to a therapeutically effective amount of Transforming Growth Factor-β3 (TGF-β3) and of an antibody that inhibits Her-2/neu receptor function, wherein the antibody that inhibits Her-2/neu receptor function binds a Her-2/neu receptor epitope to which monoclonal antibody 4D5 (ATCC CRL 10463) binds.

13. The method claim 12 wherein the antibody comprises an amino acid sequence from a complementarity determining region of monoclonal antibody 4D5 (ATCC CRL 10463) and an amino acid sequence from a framework region of a human antibody.

14. A method of treating breast cancer in a mammal having a breast cancer that overexpresses Her-2/neu comprising administering to the mammal a therapeutically effective amount of Transforming Growth Factor-β1 (TGF-β1) and of an antibody that inhibits Her-2/neu receptor function, wherein the antibody that inhibits Her-2/neu receptor function binds a Her-2/neu receptor epitope to which monoclonal antibody 4D5 (ATCC CRL 10463) binds.

15. The method of claim 14 wherein the antibody comprises an antigen-binding region of monoclonal antibody 4D5 (ATCC CRL 10463).

16. A method of treating breast cancer in a mammal having a breast cancer that overexpresses Her-2/neu comprising administering to the mammal a therapeutically effective amount of Transforming Growth Factor-β2 (TGF-β2) and of an antibody that inhibits Her-2/neu receptor function, wherein the antibody that inhibits Her-2/neu receptor function binds a Her-2/neu receptor epitope to which monoclonal antibody 4D5 (ATCC CRL 10463) binds.

17. The method of claim 16 wherein the antibody comprises an antigen-binding region of monoclonal antibody 4D5 (ATCC CRL 10463).

18. A method of treating breast cancer in a mammal having a breast cancer that overexpresses Her-2/neu comprising administering to the mammal a therapeutically effective amount of Transforming Growth Factor-β3 (TGF-β3) and of an antibody that inhibits Her-2/neu receptor function, wherein the antibody that inhibits Her-2/neu receptor function binds a Her-2/neu receptor epitope to which monoclonal antibody 4D5 (ATCC CRL 10463) binds.

19. The method of claim 18 wherein the antibody comprises an antigen-binding region of nionoclonal antibody 4D5 (ATCC CRL 10463).

* * * * *